US011195279B1

(12) United States Patent
Beck et al.

(10) Patent No.: US 11,195,279 B1
(45) Date of Patent: Dec. 7, 2021

(54) SYSTEMS AND METHODS FOR TRAINING A STATISTICAL MODEL TO PREDICT TISSUE CHARACTERISTICS FOR A PATHOLOGY IMAGE

(71) Applicant: PathAI, Inc., Boston, MA (US)

(72) Inventors: Andrew H. Beck, Brookline, MA (US); Aditya Khosla, Watertown, MA (US)

(73) Assignee: PathAI, Inc., Boston, MA (US)

( * ) Notice: Subject to any disclaimer, the term of this patent is extended or adjusted under 35 U.S.C. 154(b) by 56 days.

(21) Appl. No.: 16/841,827

(22) Filed: Apr. 7, 2020

Related U.S. Application Data

(63) Continuation of application No. 16/001,855, filed on Jun. 6, 2018, now Pat. No. 10,650,520.

(Continued)

(51) Int. Cl.
*G06T 7/00* (2017.01)
*G06T 7/194* (2017.01)
*G06N 5/04* (2006.01)
*G06F 16/58* (2019.01)
*G16H 50/50* (2018.01)
*G16H 10/20* (2018.01)
(Continued)

(52) U.S. Cl.
CPC ........ *G06T 7/0014* (2013.01); *G06F 16/5866* (2019.01); *G06K 9/6256* (2013.01); *G06K 9/6265* (2013.01); *G06N 5/046* (2013.01); *G06T 7/194* (2017.01); *G16H 10/20* (2018.01); *G16H 50/20* (2018.01); *G16H 50/50* (2018.01); *G06T 2207/20081* (2013.01); *G06T 2207/30004* (2013.01)

(58) Field of Classification Search
CPC ..... G16H 10/20; G06F 16/5866; G06N 5/046
See application file for complete search history.

(56) References Cited

U.S. PATENT DOCUMENTS 9,031,306 B2   5/2015  Parvin et al.
10,121,245 B2  11/2018 Chen et al.
(Continued)

OTHER PUBLICATIONS

Beck et al., Systemic Analysis of Breast Cancer Morphology Uncovers Stromal Features Associated with Survival. Science Translational Medicine. Nov. 9, 2011;3(108):1-12.

(Continued)

*Primary Examiner* — Edward Park
(74) *Attorney, Agent, or Firm* — Wolf, Greenfield & Sacks, P.C.

(57) ABSTRACT

In some aspects, the described systems and methods provide for a method for training a statistical model to predict tissue characteristics for a pathology image. The method includes accessing annotated pathology images. Each of the images includes an annotation describing a tissue characteristic category for a portion of the image. A set of training patches and a corresponding set of annotations are defined using an annotated pathology image. Each of the training patches in the set includes values obtained from a respective subset of pixels in the annotated pathology image and is associated with a corresponding patch annotation determined based on an annotation associated with the respective subset of pixels. The statistical model is trained based on the set of training patches and the corresponding set of patch annotations. The trained statistical model is stored on at least one storage device.

20 Claims, 13 Drawing Sheets

Related U.S. Application Data

(60) Provisional application No. 62/515,772, filed on Jun. 6, 2017, provisional application No. 62/515,779, filed on Jun. 6, 2017, provisional application No. 62/515,795, filed on Jun. 6, 2017.

(51) Int. Cl.
*G06K 9/62* (2006.01)
*G16H 50/20* (2018.01)

(56) References Cited

U.S. PATENT DOCUMENTS

| | | | |
|---|---|---|---|
| 10,275,891 B2 | 4/2019 | Jalali et al. | |
| 10,650,520 B1 | 5/2020 | Beck et al. | |
| 10,650,929 B1 | 5/2020 | Beck et al. | |
| 2010/0088264 A1* | 4/2010 | Teverovskiy | G16H 50/20 706/46 |
| 2013/0294676 A1 | 11/2013 | Parvin et al. | |
| 2015/0110381 A1 | 4/2015 | Parvin et al. | |
| 2015/0247149 A1 | 9/2015 | Feldstein et al. | |
| 2017/0270239 A1* | 9/2017 | Grafstrom | G16B 5/20 |
| 2017/0270666 A1 | 9/2017 | Barnes et al. | |
| 2017/0309021 A1 | 10/2017 | Barnes et al. | |
| 2017/0357844 A1* | 12/2017 | Comaniciu | G06K 9/00536 |
| 2018/0365824 A1 | 12/2018 | Yuh et al. | |
| 2019/0180153 A1 | 6/2019 | Buckler et al. | |
| 2019/0183429 A1 | 6/2019 | Sung et al. | |
| 2019/0384047 A1 | 12/2019 | Johnson et al. | |

OTHER PUBLICATIONS

Gurcan et al., Histopathological Image Analysis: A Review. IEEE Rev Biomed Eng. 2009;2:147-71.

Litjens et al., A Survey on Deep Learning in Medical Image Analysis. Diagnostic Image Analysis Group. Radboud University Medical Center. Mijmegen, The Netherlands. Jun. 4, 2017; 38 pages.

Madabhushi et al., Image analysis and machine learning in digital pathology: Challenges and opportunities. Medical Image Analysis. 2016;33:170-5.

Wang et al., Deep Learning for Identifying Metastatic Breast Cancer. Jun. 18, 2016; 6 pages. [Last accessed Jul. 13, 2018 from http://camelyon16.grand-challenge.org.].

U.S. Appl. No. 16/001,855, filed Jun. 6, 2018, Beck et al.
U.S. Appl. No. 16/001,862, filed Jun. 6, 2018, Beck et al.
U.S. Appl. No. 16/001,836, filed Jun. 6, 2018, Beck et al.
U.S. Appl. No. 16/857,079, filed Apr. 23, 2020, Beck et al.

\* cited by examiner

100

SYSTEMS AND METHODS FOR TRAINING A STATISTICAL MODEL TO PREDICT TISSUE CHARACTERISTICS FOR A PATHOLOGY IMAGE

CROSS REFERENCE TO RELATED APPLICATIONS

This Application is a Continuation of U.S. patent application Ser. No. 16/001,855, entitled "SYSTEMS AND METHODS FOR TRAINING A STATISTICAL MODEL TO PREDICT TISSUE CHARACTERISTICS FOR A PATHOLOGY IMAGE," and filed on Jun. 6, 2018, which claims priority under 35 U.S.C. § 119(e) to U.S. Provisional Application Ser. No. 62/515,772, entitled "DATA-DRIVEN DIAGNOSTIC METHODS" and filed on Jun. 6, 2017, U.S. Provisional Application Ser. No. 62/515,779, entitled "COMBINED USE OF IMAGE AND MOLECULAR DATA FOR PATHOLOGY" and filed on Jun. 6, 2017, and U.S. Provisional Application Ser. No. 62/515,795, entitled "PATHOLOGY ANALYSIS SYSTEMS AND METHODS" and filed on Jun. 6, 2017, each of which is herein incorporated by reference in its entirety.

BACKGROUND

Cancer is one of the leading causes of death in the United States. Each year over 1.5 million people are newly diagnosed with cancer in the United States alone. Over 500,000 Americans die from cancer annually, and many more suffer from it. The burden of the disease is not limited to cancer patients but extends to their families and social circles. The loss of a loved one can be devastating, and even when the cancer patient survives, the uncertainty is emotionally trying. Cancer exacts an economic toll as well: the estimated direct medical costs for cancer treatment in the United States in 2014 were $87.8 billion, and some sources project that this number could exceed $200 billion by 2020. In addition to cancer, other burdensome diseases, such as Alzheimer's disease, Parkinson's disease, diabetes, cystic fibrosis, sickle cell anemia, and autoimmune diseases, continue to affect the lives of millions of people, either directly or indirectly, every year.

While significant resources have been dedicated to treating such diseases, in almost all cases, early and accurate detection is crucial to successful outcomes. Furthermore, because many treatments are painful and carry their own set of patient risks, accurate diagnoses are essential before beginning treatment. It is for that reason that preliminary screens such as mammograms, prostate exams, and pap tests are followed up with tissue biopsies when abnormalities are found.

SUMMARY

In some aspects, systems and methods are described for training and/or using a statistical model to annotate pathology images with one or more tissue characteristics. For example, the described systems and methods may be used to examine images of lymph nodes to determine whether or not those tissues contain indicia of breast cancer.

In various aspects, the training data for the statistical model may include pathology images, such as tissue images, labeled by pathologists to identify regions of cancer and regions of normal cells. The tissue images may be microscopic images of tissue samples (e.g., tissue slices). A set of training patches for each pathology image from the training data may be defined and provided as input to the statistical model for training. Each training patch may include one or more annotations describing one of the tissue characteristic categories. The statistical model may be trained on the set of training patches and the corresponding set of annotations. In some embodiments, the annotations may be assigned by a pathologist or other medical professional. In some embodiments, the annotations may be assigned based on the output of the statistical model.

In some embodiments, examples of training patches for which the model classified incorrectly are identified, and the model is retrained on these difficult training patches to improve the performance of the model. In some embodiments, the statistical model may be used to assign annotations to one or more portions of a pathology image. Inaccurate annotations assigned by processing the pathology image using the statistical model may be identified, e.g., by a pathologist, and corresponding subsets of training data may be provided to the statistical model for retraining, so that the performance of the statistical model may be improved.

In some aspects, the described systems and methods optionally provide for training and using a model, such as a classifier, to predict prognostic information, such as patient survival time, using feature values extracted from the annotated pathology images. For example, the trained model may be used to predict how well a given patient will respond to certain treatments based on the predicted prognostic information.

In some embodiments, once a statistical model is trained to predict tissue characteristic categories for a pathology image, the pathology image may be fully annotated by processing the image using the statistical model. The fully annotated pathology image may be analyzed to determine values for one or more features. These feature values and corresponding patient prognostic information may be provided as input training data to a model (e.g., a random forest, a support vector machine, regression, a neural network, or another suitable model) to the model to predict prognostic information, such as patient survival time, from sample data for a patient.

In some embodiments, the training data may include known outcomes of individuals from whom the training data, e.g., the tissue images, was obtained. The known outcomes may be, for example, one or more of tumor metastasis, tumor progression, or patient survival related to a cancer. Examples of cancer that may be related with known outcomes include, but are not limited to, breast cancer, lung cancer, ovarian cancer, uterine cancer, cervical cancer, vaginal cancer, colorectal cancer, prostate cancer, skin cancer, or pancreatic cancer. The known outcomes may alternatively be related to another genetically-based disease, such as Alzheimer's disease, Parkinson's disease, diabetes, cystic fibrosis, sickle cell anemia, or an autoimmune disease.

In some embodiments, the model is trained on data from patients in a treatment group of a clinical trial. The trained model is then used to predict survival data for another treatment group of the clinical trial. The performance of the model to be able to accurately predict survival data for patients in the other treatment group is analyzed to determine its effectiveness in correctly identifying a subset of patients that may benefit from the experimental treatment studied in the clinical trial. In some embodiments, the trained model is used to predict an expected benefit of an experimental treatment for candidate patients in a new clinical trial. The information provided as output from the trained model may be used to select patients for the new clinical trial that are likely to benefit from the experimental treatment, thus improving the chances that the new clinical trial will be successful.

In some aspects, the described systems and methods provide for a method for training a statistical model to predict tissue characteristics for a pathology image. The method includes accessing annotated pathology images. Each of the images includes an annotation describing a tissue characteristic category for a portion of the image. A set of training patches and a corresponding set of annotations are defined using an annotated pathology image. Each of the training patches in the set includes values obtained from a respective subset of pixels in the annotated pathology image and is associated with a corresponding patch annotation determined based on an annotation associated with the respective subset of pixels. The statistical model is trained based on the set of training patches and the corresponding set of patch annotations. The trained statistical model is stored on at least one storage device.

In some embodiments, an unannotated portion of the annotated pathology image is processed, using the trained statistical model, to predict an annotation of a tissue characteristic category for the unannotated portion of the image. The predicted annotation is presented to a user via a user interface. An indication of whether the predicted annotation is accurate is received via the user interface. If the indication specifies that the predicted annotation is accurate, the unannotated portion of the image is associated with the predicted annotation.

In some embodiments, if the indication specifies that the predicted annotation is not accurate, the predicted annotation is updated based on the received indication. A set of training patches is redefined from the annotated pathology images. The statistical model is retrained based on the redefined set of training patches and the respective annotations. The retrained statistical model is stored on the storage device. In some embodiments, the updated annotation has a category determined based on the received indication. In some embodiments, the category for the updated annotation is a background category.

In some embodiments, defining the set of training patches from the annotated pathology images comprises including in the set of training patches, at least some training patches from each of the plurality of tissue characteristic categories. In some embodiments, the set of training patches includes training patches uniformly distributed across all of the plurality of tissue characteristic categories. In some embodiments, a distribution across the tissue characteristic categories in the set of training patches differs from a distribution across the tissue characteristic categories of annotations in the annotated pathology images.

In some embodiments, defining the set of training patches from the annotated pathology images comprises including in the set of training patches a training patch associated an annotation for a background category. The training patch is located a radius of pixels from an annotation having a category other than the background category.

In some embodiments, defining the set of training patches from the plurality of annotated pathology images comprises including in the set of training patches at least some training patches having an annotation at a center of the respective training patch.

In some embodiments, a dimension of each of the training patches in the set is larger than a corresponding dimension of input to the statistical model. The additional pixels in each of the training patches in the set are included when randomly resampling the respective training patch for data augmentation.

In some embodiments, the statistical model includes a convolutional neural network including a plurality of layers, and there is no padding applied to an output of any layer of the plurality of layers.

In some embodiments, the statistical model includes a convolutional neural network including a plurality of layers, and at least one of the plurality of layers, having input of size N*N, a convolution filter of size K, and a stride S, is aligned such that (N−K)/S is an integer.

In some embodiments, the tissue characteristic categories includes one or more categories selected from a group including cancer epithelium, cancer stroma, normal tissue, necrosis, lymphoid, macrophage, lymphocyte, fibroblast, plasma cell, pulmonary macrophage, melanoma, pigmented macrophage, endothelial cell, mitotic figure, nucleoli, nuclear pleomorphism, nerve, adipocyte, peri-neural invasion, epithelial and epithelial tubule formation, and other suitable tissue characteristic categories.

In some embodiments, the annotated pathology images are magnified to create a magnified set of pathology images. A second set of training patches is defined from the magnified set of annotated pathology images. A second statistical model is trained based on the second set of training patches and respective annotations. The trained second statistical model is stored on the storage device. In some embodiments, the output of the second trained statistical model is combined with the output of the trained statistical model described above using a logical AND operation or a logical OR operation.

In some aspects, the described systems and methods provide for a method for predicting tissue characteristics for a pathology image. A statistical model trained on multiple annotated pathology images is used. Each of the training pathology images includes an annotation describing tissue characteristics for one or more portions of the image. The method includes accessing a pathology image for predicting tissue characteristics. A trained statistical model is retrieved from a storage device. The statistical model is trained on a set of training patches and a corresponding set of patch annotations derived from an annotated pathology image. Each of the training patches in the set includes values obtained from a respective subset of pixels in the annotated pathology image and is associated with a corresponding patch annotation determined based on an annotation associated with the respective subset of pixels. A set of patches is defined from the pathology image. Each of the patches in the set includes a subset of pixels from the corresponding pathology image. The set of patches is processed using the trained statistical model to predict respective annotations for each patch in the set. The predicted annotations are stored on the storage device.

In some embodiments, a predicted annotation is presented to a user via a user interface. An indication of whether the predicted annotation is accurate is received via the user interface. If the indication specifies that the predicted annotation is accurate, a portion of the pathology image is associated with the predicted annotation. The association of the portion of the pathology image with the predicted annotation is stored on the storage device.

In some embodiments, the trained statistical model includes a convolutional neural network including a plurality of layers, and there is no padding applied to an output of any layer of the plurality of layers.

In some embodiments, the trained statistical model includes a convolutional neural network including a plurality of layers, and at least one of the plurality of layers, having input of size N*N, a convolution filter of size K, and a stride S, is aligned such that (N−K)/S is an integer.

In some embodiments, a second trained statistical model is retrieved from the storage device. The second trained statistical model is trained on a set of training patches and a corresponding set of patch annotations derived from a magnified annotated pathology image. The accessed pathology image is magnified to create a magnified pathology image. A second set of patches is defined from the magnified pathology image. The set of patches is processed, using the second trained statistical model, to predict respective annotations for each patch in the set. In some embodiments, the output of the second trained statistical model is combined with the output of the trained statistical model described above using a logical AND operation or a logical OR operation.

In some embodiments, a portion of the pathology image is associated with a predicted annotation. The association of the portion of the pathology image with the predicted annotation is stored on the storage device. Values for one or more features are extracted from the annotated pathology image.

In some embodiments, the one or more features are selected from a group including area of epithelium, area of stroma, area of necrosis, area of cancer cells, area of macrophages, area of lymphocytes, number of mitotic figures, average nuclear grade, average distance between fibroblasts and lymphocytes, average distance between immunohistochemistry-positive macrophages and cancer cells, standard deviation of nuclear grade, average distance between blood vessels and tumor cells. In some embodiments, a model is trained based on the extracted values for the one or more features to predict an entity of interest. In some embodiments, the entity of interest is selected from a group including survival time, drug response, patient level phenotype/molecular characteristics, mutational burden, tumor molecular characteristics, transcriptomic features, protein expression features, patient clinical outcomes, and other suitable entities of interest.

In some embodiments, the model is trained on the extracted feature values by accessing annotated pathology images, training the model based on the entity of interest and the extracted values for the features from each of the annotated pathology images, and storing the trained model on the storage device. Each of the annotated pathology images is associated with the entity of interest, each of the annotated pathology images includes an annotation for a portion of the image, and values are extracted for the features from each of the annotated pathology images.

In some aspects, the described systems and methods provide for a method for training a model to predict survival time for a patient. The method includes accessing annotated pathology images associated with a first group of patients in a clinical trial. Each of the annotated pathology images is associated with survival data for a respective patient. Each of the annotated pathology images includes an annotation describing a tissue characteristic category for a portion of the image. Values for one or more features are extracted from each of the annotated pathology images. A model is trained based on the survival data and the extracted values for the features. The trained model is stored on a storage device.

In some embodiments, the clinical trial is a randomized controlled trial, and the first group of patients belong to an experimental treatment group of the randomized controlled trial. In some embodiments, values for features extracted from annotated pathology images associated with a second group of patients are processed using the trained model. The values are processed to predict survival data for patients in the second group of patients. The patients in the second group of patients belong to a control treatment group of the randomized controlled trial.

In some embodiments, a first prognostic performance of the trained model for the experimental treatment group is determined based on the predicted survival data for the patients in the first group of patients and respective survival data. A second prognostic performance of the trained model for the control treatment group is determined based on predicted survival data for the patients in the second group of patients and respective survival data. A specificity of a prognostic power of the trained model is determined by comparing the first prognostic performance of the trained model for the experimental treatment group and the second prognostic performance of the trained model for the control treatment group. The specificity of the prognostic power of the trained model includes a likelihood that the model will correctly identify of a subset of patients that benefit from experimental treatment. In some embodiments, comparing the first prognostic performance and the second prognostic performance includes performing subset survival analyses using respective predicted survival data from the experimental treatment group and the control treatment group.

In some embodiments, the extracted values for the features are processed, using the trained model, to predict respective survival data for the first group of patients. The first group of patients belong to an experimental treatment group. Based on the predicted survival data, a subset of the first group of patients that responded to the experimental treatment is selected. In some embodiments, based on the predicted survival data, a subset of the features indicative of the subset of the first group of patients that responded to the experimental treatment is selected.

In some embodiments, values for features extracted from annotated pathology images associated with a second group of patients are processed, using the trained model, to predict survival data for the patients in the second group of patients. The second group of patients belongs to a treatment group in another clinical trial. A subset of the second group of patients that are expected to respond to treatment is selected.

In some embodiments, the features are selected from a group including area of epithelium, area of stroma, area of necrosis, area of cancer cells, area of macrophages, area of lymphocytes, number of mitotic figures, average nuclear grade, average distance between fibroblasts and lymphocytes, average distance between immunohistochemistry-positive macrophages and cancer cells, standard deviation of nuclear grade, average distance between blood vessels and tumor cells.

In some embodiments, the trained model includes one or more of a generalized linear model, a random forest, a support vector machine, a gradient boosted tree, and another suitable model.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence is intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

DETAILED DESCRIPTION

Conventionally, tissue biopsies rely on human analysis of stained tissue samples using a microscope and techniques primarily developed over a hundred years ago. Pathologists study and identify certain established characteristics in tissue samples that are indicative of disease, such as cancer. Pathologists typically undergo years of specialized training in diagnostic analysis of tissue samples but, their interpretation of samples is still subject to human error. Furthermore, reliance on specialized human analysis poses a significant rate limitation and incurs great expense in diagnosing disease from tissue samples. Additionally, current techniques still rely on identifying patterns and features detectable by the human eye and require progression of the disease to a level at which those features are identifiable.

Figure 1:
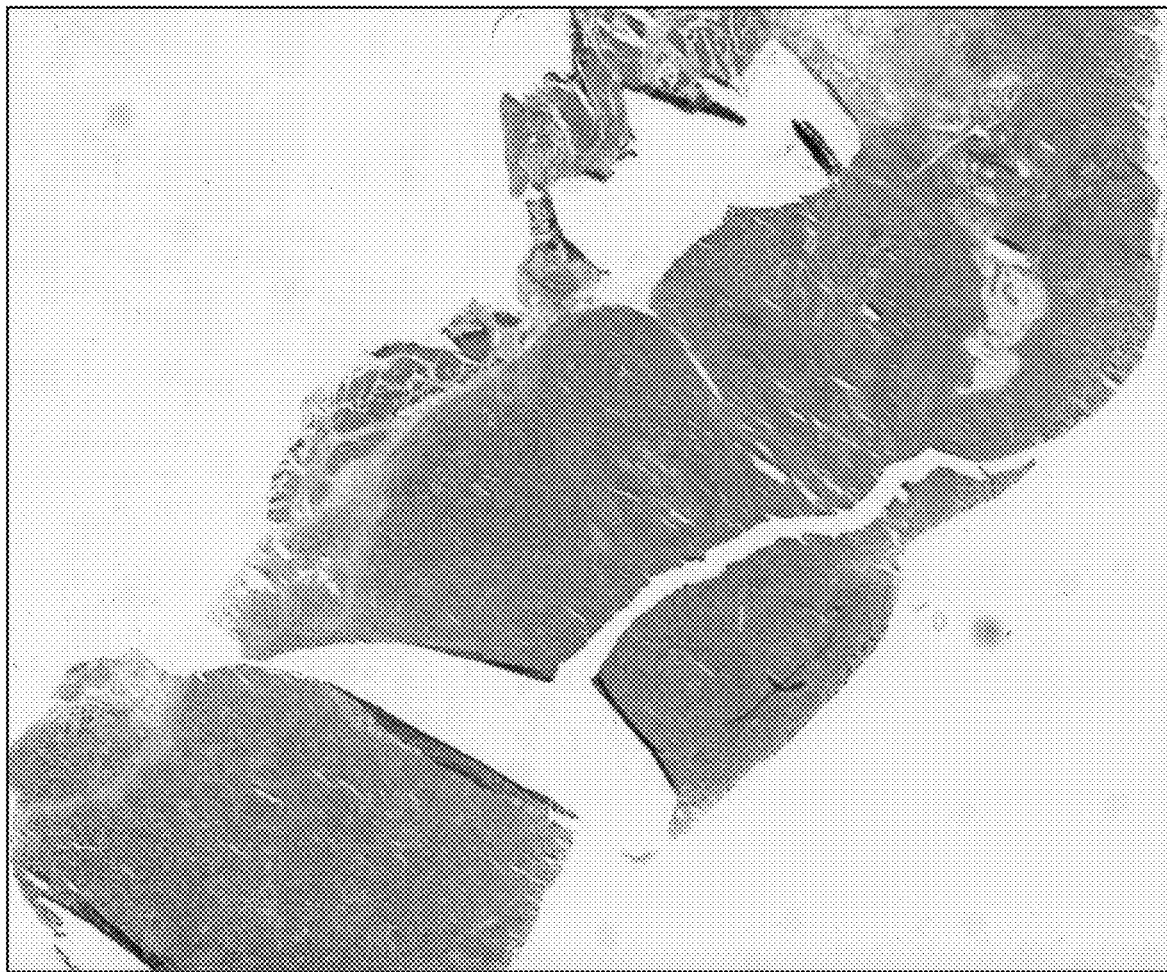
FIG. 1 shows a tissue sample image in accordance with some embodiments of the technology described herein.

FIG. 1 shows a tissue sample image 100 in accordance with some embodiments of the technology described herein. Tissue images annotated in accordance with the techniques described herein may be microscopic images of tissue samples extracted from a patient. The tissue images may be obtained by using an imaging instrument to create images of slides on which tissue slices are mounted. The tissue slices mounted on the slides may have been taken from tissue samples, such as biopsy or autopsy specimens. The tissue samples may have been processed prior to capturing of images. For example, the tissue samples may have been fixed, stained, labeled, washed, or dehydrated. The samples may be taken from any tissue that indicates the presence or absence of a pathological condition. For example, the tissue image may include a portion of a tumor. The image may be of a tissue that provides evidence of the presence or absence of a disease or condition, such as cancer, Alzheimer's disease, Parkinson's disease, diabetes, cystic fibrosis, sickle cell anemia, or an autoimmune disease. For example and without limitation, the tissue may be from a tumor or from the liver, lung, breast, ovary, uterus, cervix, vagina, testicle, spleen, lymph node, bladder, kidney, brain, esophagus, stomach, intestine, gall bladder, mouth, lip, nose, pancreas, prostate, colon, skin, or any other organ that may be suspected of having a tumor.

Tissue samples may include biopsied tissue obtained, for example, through core needle biopsy. The samples may be paraffin-embedded and may be sectioned into slices prior to staining. Tissue samples may be stained using any stain selected to highlight cellular structures or other features of interest useful in tissue analysis. The tissue samples may, for example, be prepared by hematoxylin and eosin stain (H&E stain). Examples of general staining methods include, but are not limited to, hematoxylin and eosin (H&E), trichrome, periodic acid Schiff (PAS), autoradiography, enzyme histochemistry, immuno-fluorescence, and immunohistochemistry. Specific stains include, but are not limited to, acid fuchsin, Aldehyde Fuchsin, Alician Blue, Alizarin Red S, Alkaline Phosphatase, aniline blue, Azan Stain, biebrich scarlet, Bielschowsky Stain, Cajal Stain, chromotrope 2R, Congo Red, Cresyl Violet, Eosin, fast green FCF, Fontana-Masson, Giemsa Stain, Golgi Stain, Gomori Trichrome, Heidenhain's AZAN trichrome stain, Hematoxylin, Iron Hematoxylin, light green SF yellowish, Luna Stain, Luxol Fast Blue, Mallory Trichrome, martius yellow, Masson Trichrome, Melanin Stains, methyl blue, milling yellow, Movat's Pentachrome, Mucicarmine, Mucin Stains, Myloperoxidase (MPO), Nissl Stains, Nuclear Fast Red, Oil Red O, orange G, Orcien Stain, Osmium Tetroxide, Papanicolaou Stain, Perl's Iron Stain, phloxine, Phosphotungstic Acid-Hematoxylin (PTAH), picric acid, PicroSirius Red (polarized), ponceau 6R, Prussian Blue, Reticular Fiber Stain, Romanowsky Stains, Safranin 0, Schmorl's Stain, Silver Stains, Sudan Stains, Tartrazine, tartrazine, Toluidine Blue, Van Gieson, Verhoeff Stain, Von Kassa Stain, water blue, Weigert's Elastic Stain, Wright's Stain, and xylidine ponceau.

The tissue samples may be immune-stained with anticytokeratin antibody. The tissue samples may be prepared by yet other methods. For example, a tissue sample may be prepared by Papanicolaou stain (Pap stain). A sample could optionally be labeled by antibodies or probes, e.g., either of which could be fluorescently labeled or conjugated to elemental isotopes for mass spectrometry. Tissue staining may comprise immunohistochemistry staining using, for example, labelled antibodies targeting proteins of interest or primary followed by secondary antibodies where the primary antibodies target proteins of interest and the secondary antibodies target the primary antibodies and carry, for example, a fluorescent or otherwise reporter detectable through known imaging techniques. Tissue staining such as immunohistochemistry may be performed on an automated platform such as those available from Ventana Medical Systems, Inc. (Tucson, Ariz.). Tissue sample images may be captured using an imaging instrument such as a microscope and digital camera and corresponding software.

Any suitable imaging instrument may be used to obtain a tissue image from a tissue sample on a slide. In some embodiments. a suitable imaging instrument includes an Olympus BX41 microscope in combination with a DP21 2 MP camera and CellSens software all available from Olympus Corporation (Center Valley, Pa.). Another suitable imaging instrument includes the Aperio ScanScope CS-0, Aperio AT2, and Aperio eSlide manager and web browser all available from Leica Biosystems, Inc. (Buffalo Grove, Ill.). Stained tissue images may be acquired using, for example, a high resolution whole-slide scanner such as the Nanozoomer Whole Slide Scanner from Hamamatsu (Hamamatsu City, Shizuoka Pref., Japan). Once tissue sample images are acquired, either for training data or from a test sample, the image data may be provided to a system configured to process the image data using, for example, a statistical model.

Figure 2:
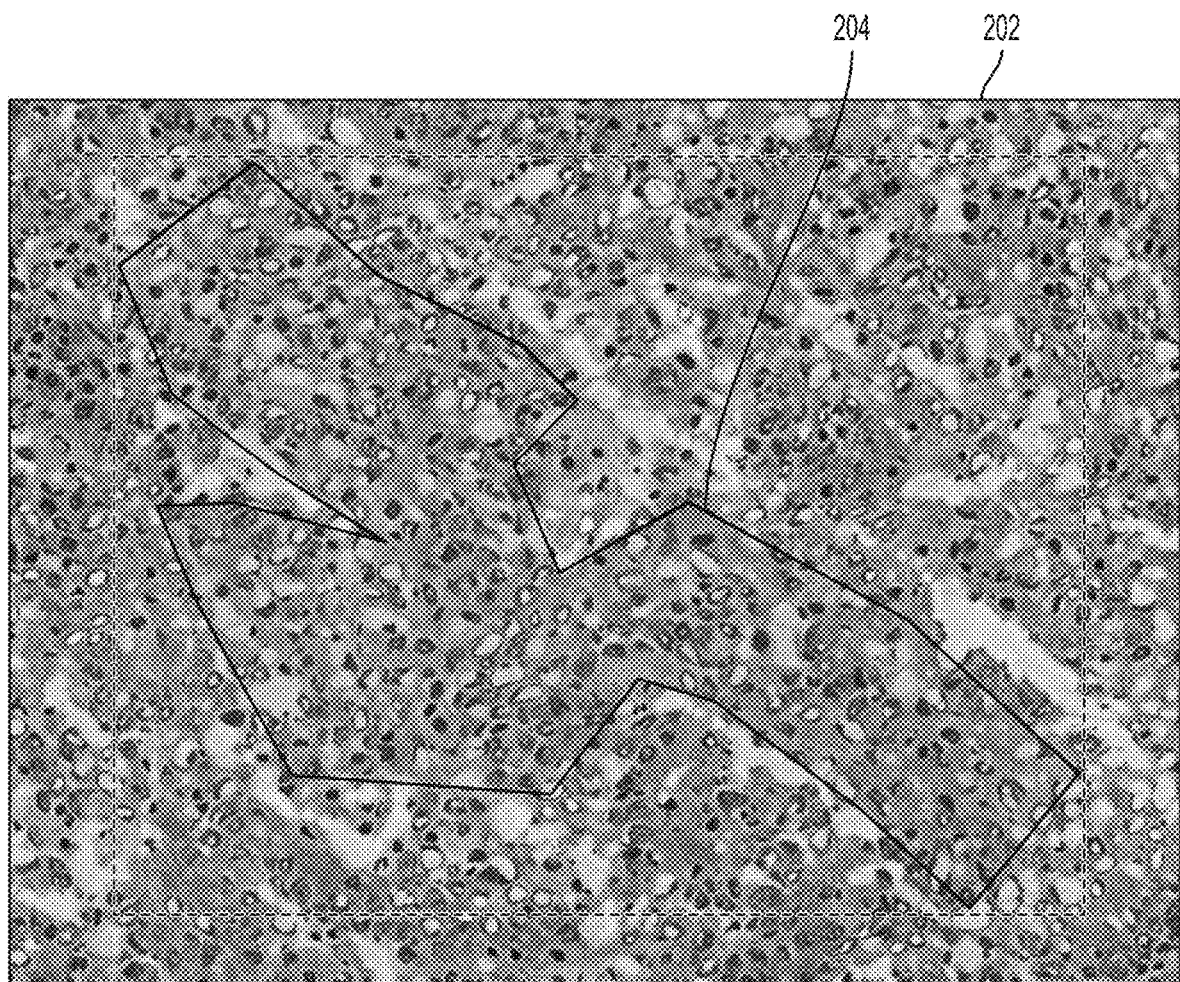
FIG. 2 shows a tissue sample image with a polygon annotation in accordance with some embodiments of the technology described herein.

FIG. 2 shows a tissue sample image 200 that has been annotated with a polygon annotation 204. The polygon annotation 204 may have been drawn, for example, by a pathologist or other medical professional to indicate a particular tissue type within the annotated region. For example, the pathologist may have drawn the polygon annotation 204 using a user interface of a computer system. The annotated tissue sample image may be used as training data for training a statistical model to predict tissue characteristics for a pathology image. For example, the statistical model may be trained to predict whether or not tissue sample images of lymph nodes contain indicia of breast cancer. Tissue sample image 200 also includes a subset of pixels in the image designated as training patch 202. Training patch 202 includes the polygon annotation 204 of a tissue characteristic category, for example, the category cancer epithelium. The size of the training patch may be selected to be a size suitable for training the statistical model. For example, the training patch 202 may be of size 222 pixels by 222 pixels or another size which is suitable for using as input training data to train a statistical model (e.g., a convolutional neural network). In some embodiments, a tissue sample image may include a large number of pixels (e.g., 50,000 pixels by 50,000 pixels), and multiple training patches having smaller numbers of pixels (e.g., 222 pixels by 222 pixels) may be defined within the tissue sample image as a set of training patches.

The training patches in the set may include annotations of tissue characteristics from, e.g., a pathologist. In some embodiments, less than 1% of the sample image is initially annotated. In some embodiments, less than 5% of the sample image is initially annotated. Each of the annotations is associated with a tissue characteristic category, examples of which include, but are not limited to, cancer epithelium, cancer stroma, background, normal tissue, necrosis, lymphoid, macrophage, lymphocyte, fibroblast, plasma cell, pulmonary macrophage, melanoma, pigmented macrophage, endothelial cell, mitotic figure, nucleoli, nuclear pleomorphism, nerve, adipocyte, peri-neural invasion, epithelial and epithelial tubule formation, or another suitable tissue characteristic category. According to one aspect, a statistical model that is trained on pathology images that are sparsely annotated by pathologists (e.g., drawn in an online application) may be capable of predicting additional annotations for other unlabeled portions of a pathology image.

In some embodiments, training patches are sampled from one or more pathology images to maintain a uniform distribution of tissue characteristic categories in the set of training patches. For example, if the statistical model is to be trained on four different categories of annotations, an equal number of training patches from each of the four categories may be sampled as training data. A statistical model trained on a set of training patches where tissue characteristic categories are uniformly distributed may provide improved prediction performance over another statistical model trained on a set of training patches with a non-uniform distribution. In some embodiments, the training patches are sampled in a distribution that differs from the distribution of annotations in the training image. In some embodiments, approximately one million training patches are included in the set. In some embodiments, the statistical model is trained on multiple pathology images, e.g., at least 50 such images. The pathology images may belong to different patients having the same disease.

The statistical model may include one or more of a support vector machine, a neural network, a convolutional neural network, a regression, a random forest, a clustering, a Bayesian network, reinforcement learning, metric learning, a genetic algorithm, or another suitable statistical model. In some embodiments, the statistical model is a convolutional neural network having input dimensions of 217 pixels by 217 pixels, whereas the training patch size is 222 pixels by 222 pixels. The additional five pixels in each dimension may be used for random resampling for data augmentation. For example, the original patch of 222 pixels by 222 pixels may be randomly resampled to generate multiple training patches of 217 pixels by 217 pixels for input to the statistical model. Augmenting the training data in this manner to provide more training patches for the statistical model to train may lead to faster training time and/or improved predictive performance.

Throughout this disclosure, a convolutional neural network is used as an example of a statistical model that may be used in accordance with some embodiments. However, it should be appreciated that other types of statistical models may alternatively be used, and embodiments are not limited in this respect. Other types of statistical models that may be used include a support vector machine, a neural network, a regression model, a random forest, a clustering model, a Bayesian network, reinforcement learning, metric learning, a genetic algorithm, or another suitable statistical model.

Figure 7:
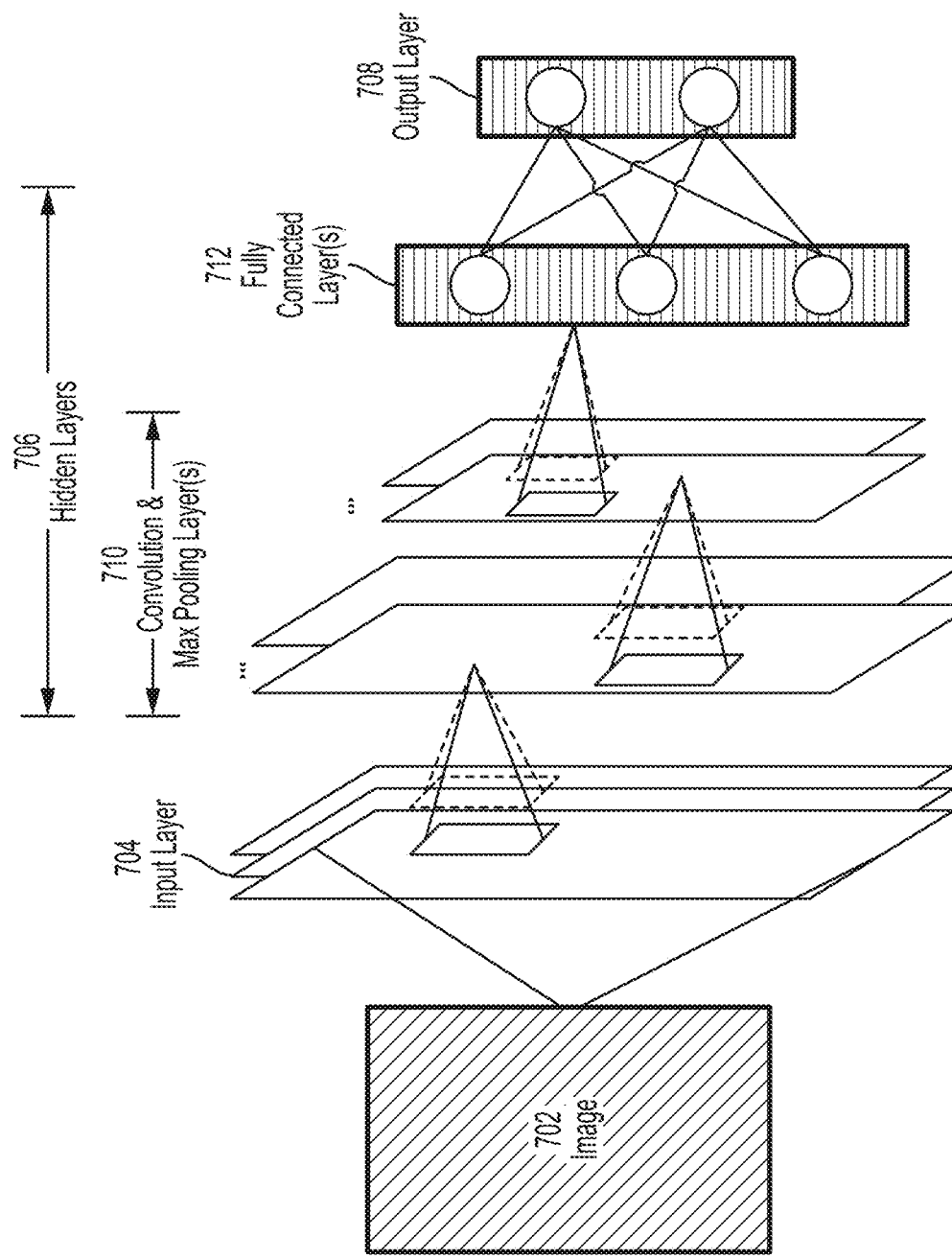
FIG. 7 schematically shows layers of a convolutional neural network in accordance with some embodiments of the technology described herein.

More details for training the convolutional neural network are provided with respect to FIG. 7.

Figure 3:
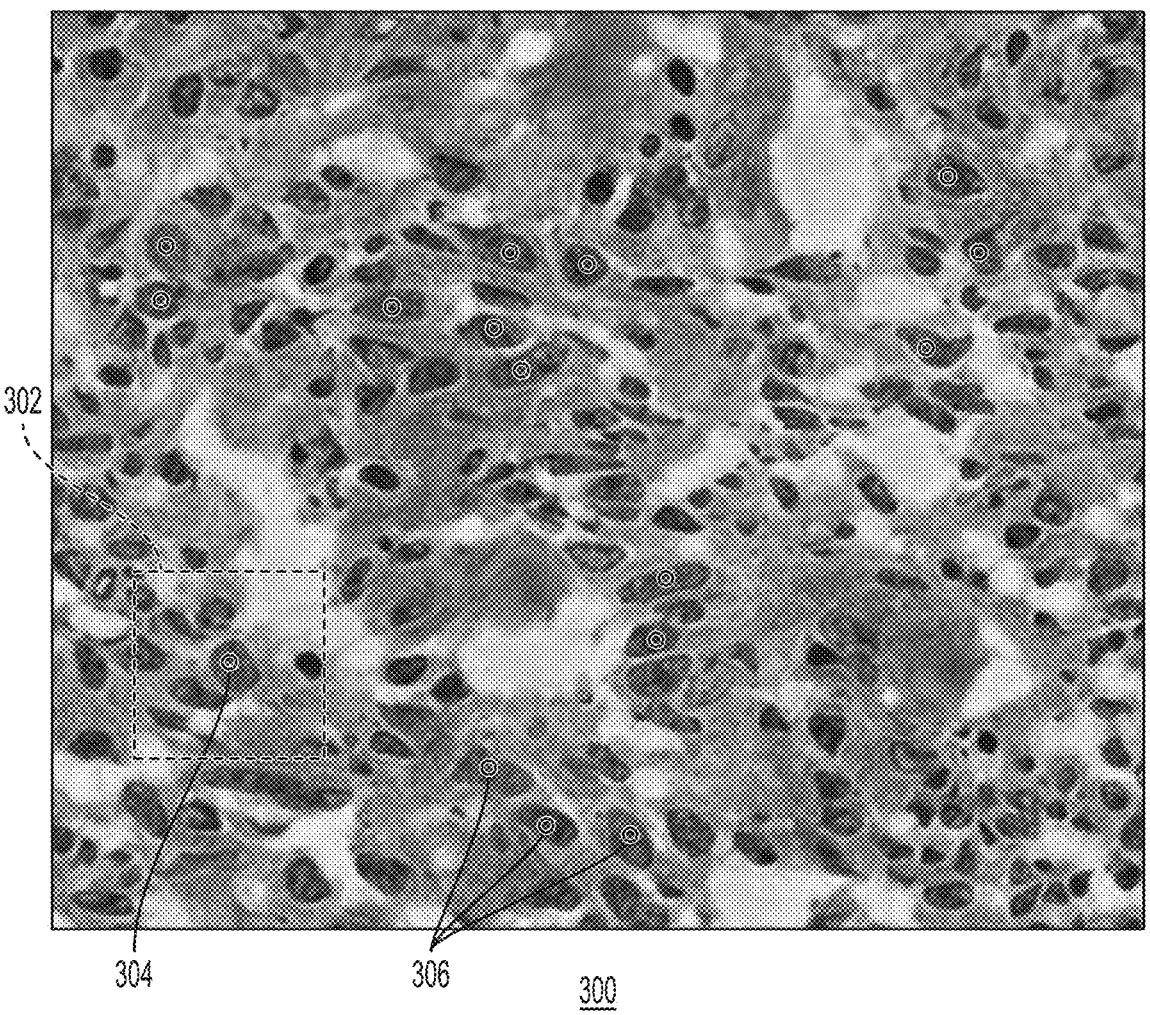
FIG. 3 shows a tissue sample image with a point annotation in accordance with some embodiments of the technology described herein.

FIG. 3 shows a tissue sample image 300 that has been annotated with point annotations, e.g., 304 and 306. Training patches that relate to annotated portions of this tissue sample image may be used as training data for training a statistical model to predict tissue characteristics for a pathology image. The statistical model may be trained in a manner similar to that described with respect to FIG. 2. As shown, sample image 300 includes training patch 302 which defines a subset of pixels associated with the point annotation 304. Training patch 302 may be selected to be a size suitable for training the statistical model. For example, the training patch 302 may be of size 102 pixels by 102 pixels, or any other size which is suitable for input to a convolutional neural network or other statistical model. More details for training the statistical model (e.g., a convolutional neural network) are provided with respect to FIG. 7.

In some embodiments, the training data includes training patches for a "background" tissue characteristic category. In order to obtain a distribution that is suitable for identifying point annotations, training patches for the background category may be added to the training data such that the training patches for this category are positioned a particular distance (e.g., a certain radius in number of pixels) from an annotated point in the image and represent background tissue that is not associated with an annotation. In some embodiments, the training data includes at least some training patches that have an annotation located at or near the center pixel of the training patch. The annotation at or near the center of the training patch may include an annotation associated with a center pixel or group of pixels including the center pixel of the training patch. Additionally or alternatively, the annotation at or near the center of the training patch may include an annotation associated with one or more pixels within a certain distance from the center pixel of the training patch. Defining training patches in this way may result in the convolutional neural network trained to output a high probability for the tissue characteristic category associated with the point annotation when the point annotation is located at or near the center of a portion of the image being processed rather than outputting the high probability when the point annotation is present in the portion of the image being processed, but is not located at or near the center pixel of the image portion. In some embodiments, the network architecture trained to predict point annotations (e.g., those described with respect to FIG. 3) may have fewer layers or nodes than the network architecture trained to predict polygon annotations (e.g., those described with respect to FIG. 2).

In some embodiments, the output of the network architecture trained to predict point annotations may be combined with the output of the network architecture trained to predict polygon annotations to obtain predictions for annotations that may be more accurate that using the output of a single network architecture. For example, a network configured to process smaller patches has access to a smaller portion of the image and hence has less context for predicting a particular point annotation for the patches being processed. Combining the output of the network configured to processes smaller patches with an output of a network that considers larger portions of the image for annotation may improve the annotation prediction due to the context that the large portion of the image provides.

Figure 4:
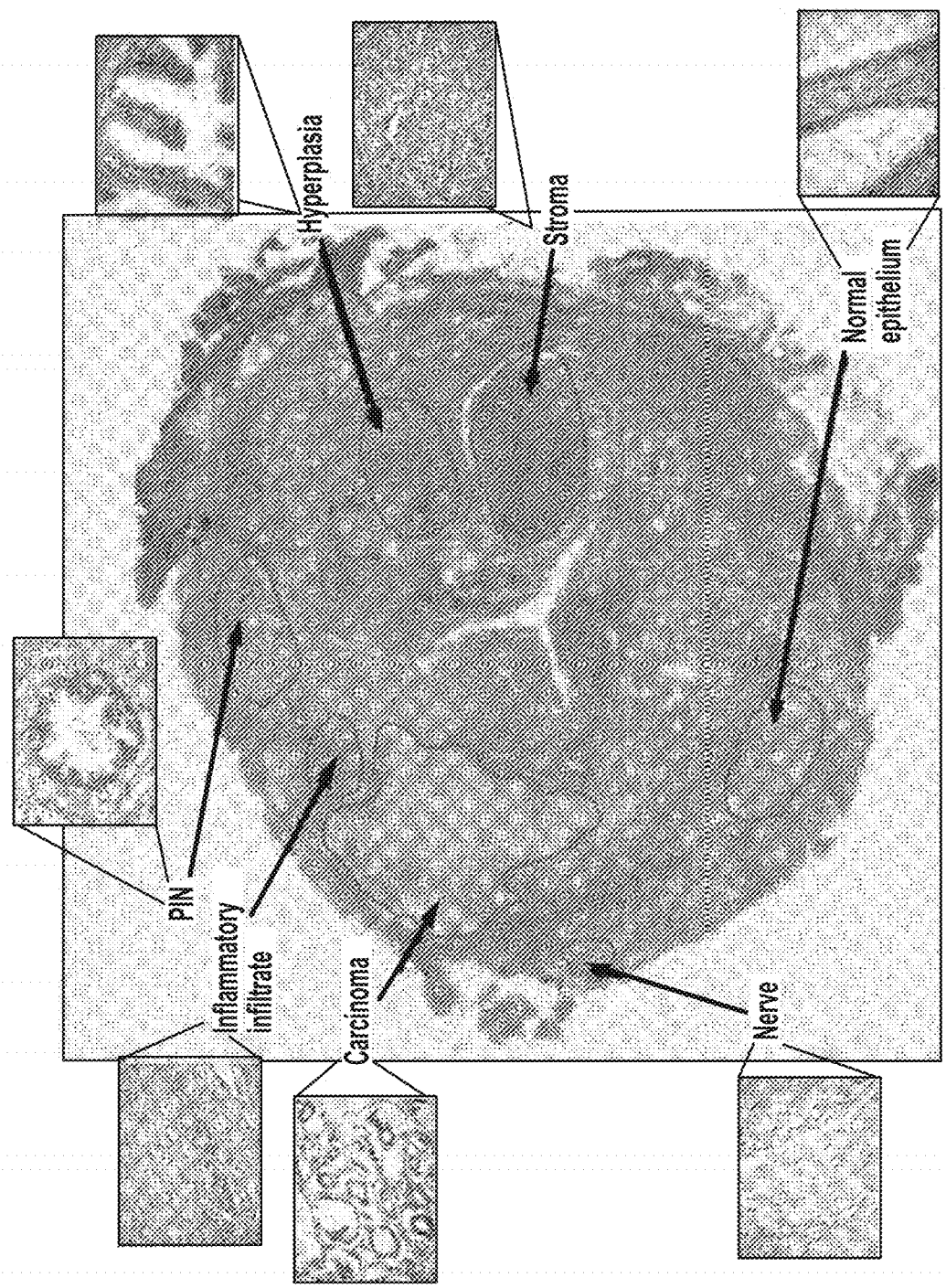
FIG. 4 shows a tissue sample image with annotations in accordance with some embodiments of the technology described herein.

FIG. 4 shows a tissue sample image 400 that has been annotated with tissue category characteristics in accordance with some embodiments of the technology described herein. Although annotations and images provided as input to a statistical model may not (or may) have the literal, human-readable format as illustrated, the annotations shown in FIG. 4 represent different types of informative annotations that may be provided as input to a statistical model for training as described above. The statistical model may be configured to identify features and associate the identified features with medical conditions. Thus where, for example, a portion of an image is annotated as, e.g., "hyperplasia," the statistical model may be configured to respond to the presence and distribution of an abundance of mitotic spindles in that portion of the image and when this response is repeated over millions of patches throughout training the statistical model may be trained to identify hyperplasia when the same pattern appears in a sample image from a patient that has not been annotated or has been sparsely annotated by a pathologist.

Figure 5:
FIG. 5 shows a heat map for a tissue sample image generated by a statistical model in accordance with some embodiments of the technology described herein.

FIG. 5 shows a heat map 500 for a tissue sample image generated by a statistical model in accordance with some embodiments of the technology described herein. The heat map 500 includes annotations for some or all tissue characteristic categories identified in the tissue sample image.

Figure 6:
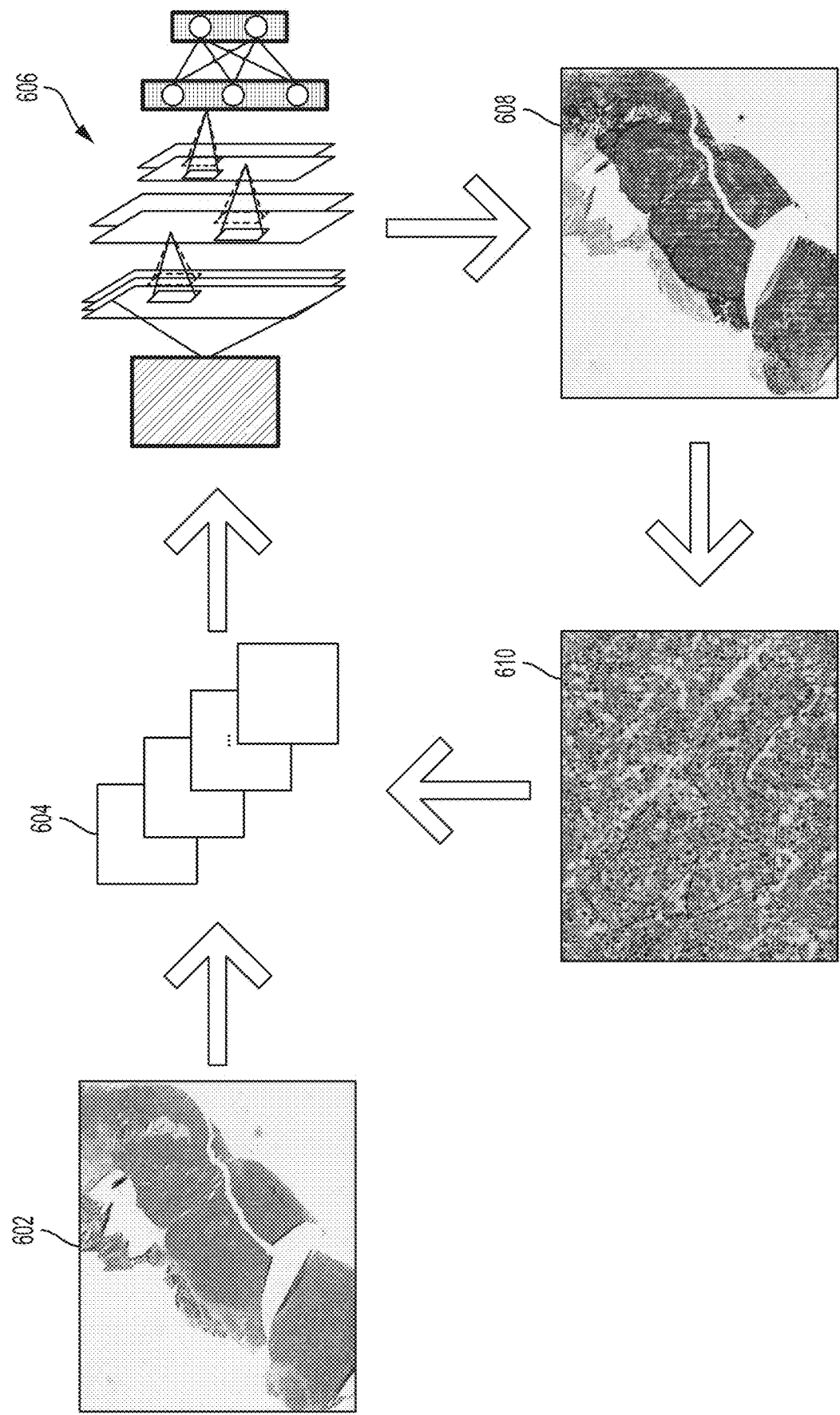
FIG. 6 shows an illustrative process for training a statistical model in accordance with some embodiments of the technology described herein.

FIG. 6 shows an illustrative process 600 for training a statistical model to generate, among other things, the heat map 500, in accordance with some embodiments of the technology described herein. At act 602, a pathology image, such as the tissue image described with respect to FIG. 1, is received. At act 604, a set of training patches, each of which includes subsets of pixels in the pathology image are defined and corresponding annotations are associated with each of the training patches in the set, as described, for example, with respect to FIGS. 2 and 3. At act 606, the set of training patches and corresponding annotations are provided as input to a statistical model, such as a convolutional neural network, to train the statistical model to predict the corresponding annotations using a supervised learning technique. In some embodiments, the statistical model is trained on the set of training patches and corresponding annotations along with other clinical metadata values, such as age, gender, clinical measurements, predicted diagnosis by pathologist, etc. These additional values may be received with the pathology image and may provide the statistical model with more information on the patient. In the case where the statistical model is a convolutional neural network, these additional values may be input at any of the layers, such as the fully-connected layers. At act 608, the trained statistical model is used to associate annotations for part or all of a pathology image using the predicted annotations, with the resultant annotated image being represented as a heat map, an example of which is shown in FIG. 5. At act 610, the annotated pathology image is supplied to an annotator, such as a pathologist, to validate the predicted annotations. If one or more of the predicted annotations is marked as inaccurate, the predicted annotations may be updated to a different tissue category as supplied by the annotator, and information related to the updated annotation may be supplied as updated training data for retraining the statistical model. If the predicted annotations are marked as accurate, the predicted annotations may be associated with corresponding portions of the pathology image, and the associations may be stored on a storage device.

In some embodiments, the statistical model may include a convolutional neural network. The convolutional neural network may be fully convolutional or may have one or more fully connected layers. In some embodiments, the statistical model may be a different type of neural network model such as, for example, a recurrent neural network, a multi-layer perceptron, and/or a restricted Boltzman machine. It should be appreciated that the statistical model is not limited to being implemented as a neural network and, in some embodiments, may be a different type of statistical model that may be used to assign labels to one or more portions of a pathology image. For example, the statistical model may be any suitable type of non-linear regression model such as a random forest regression model, a support vector regression model, or an adaptive basis function regression model. As another example, the statistical model may be a Bayesian regression model or any other suitable Bayesian Hierarchical model. In some embodiments, a neural network includes an input layer, an output layer, and one or more hidden layers that define connections from the input layer to the output layer. Each layer may have one or more nodes. For example, the neural network may include at least 5 layers, at least 10 layers, at least 15 layers, at least 20 layers, at least 25 layers, at least 30 layers, at least 40 layers, at least 50 layers, or at least 100 layers.

In some embodiments, the training data is provided to an input layer of a neural network. The training data may include a large number of training patches. The neural network may use or include a section of code or a script (e.g., in Python or Ruby) that analyzes the training patches of the images and, at each patch, provides pixel intensity values from that patch of the image to one of the nodes of the input layer. Each patch may be read into one node of the input layer until all or substantially all of image has been provided as input to the input layer. Having received the training data at the input layer, the neural network may represent the features associated with the disease at nodes of at least one hidden layer connected to the input layer. The network may interrogate slices of tumors to represent features characteristic of a condition of interest such as cancer. In some embodiments, the training data may include training patches from patients that are cancer free and the neural network may identify features that differentiate between cancer positive and cancer free tissues. FIG. 7 provides details for training a convolutional neural network in accordance with some embodiments to predict annotations for pathology images using the training data.

In some embodiments, the results are shown to one or more annotators via a user interface through which the annotator can adjust the results. The annotator may draw new polygons or points to indicate areas in the image for annotation that are different than the portions of the image associated with the predicted annotation(s). For example, if the predicted annotation associates certain pixels in the pathology image to cancer epithelium, and the annotator determines that the annotated pixels should instead be annotated as the stroma category, the annotator may draw a polygon annotation associated with the stroma category around the appropriate region of pixels in the image. In some embodiments, a network of pathologists is deployed for tasks, such as quality control, whether to input an image to be processed by the statistical model, handle requests for specific types of annotations, or validate results of outputs provided by the trained statistical model. For example, validation may be performed to ensure that the output of the trained statistical model is at least as good as an "average" pathologist.

In some implementations, a pathologist in the network may provide annotations for regions (e.g., in the form of polygon annotations) or cells (e.g., in the form of point annotations) in a pathology image. The tissue characteristic category of the annotations may be specified to the pathologist, and input requested only for annotations of the specified tissue characteristic category, to ensure that the data is collected in a structured way instead of pathologists simply inputting text, e.g., tissue characteristic category, for each annotation they provide. For example, a user interface configured to display the pathology image may provide a drop down menu and/or a selection tool that enables the pathologist to select from among a fixed set of tissue characteristic categories. The pathologist may interact with the user interface to create annotations on images that do not display the output of a trained statistical model (e.g., overlaid heat maps), or the pathologist may create the annotations on heat maps output by a statistical model in an attempt to correct errors made by the statistical model when predicting annotations for a pathology image. In another example, the pathologist may perform quality control on pathology images before they are processed. Such quality control may include, but is not limited to, determining whether the images are blurry, contain folds, or include other artifacts, such as marker stain. In yet another example, the pathologists may verify metadata associated with the image such as the organ of the tissue, the stain applied to the image, or other suitable metadata.

In some embodiments, feedback on predicted annotations from the pathologist is used to implement a training technique described further below. A typical dataset of pathology images may include example images depicting tissues that have cancer, and other tissues that are characterized as normal or healthy (e.g., do not have cancer). If a model trained to identify cancer cells predicts an annotation for cancer cells on a portion of an image that is characterized as normal tissue, it may be determined that the trained model has difficulty classifying this portion of the image and should be retrained to improve the ability of the model to accurately classify such image portions. Examples of image portions where the model output provided incorrect classifications and should be retrained on may be referred to as "hard negatives." Such examples may be added back to the training set to make the model more robust. This same technique may be applied to pathology images that contain cancer but are sparsely annotated. Instead of automatically including samples in the training data, since the slides are typically not exhaustively labeled, pathologist indications for inaccurate annotations may be used as hard negatives for retraining and improving the ability of the statistical model to make accurate annotation predictions.

FIG. 7 shows a convolutional neural network 700 that may be used to predict annotations for a pathology image in accordance with some embodiments of the technology described herein. For example, convolutional neural network 700 may be used at act 606 (FIG. 6) to predict annotations for a pathology image. The convolutional neural network may be used because such networks are suitable for analyzing visual images. The convolutional neural network may require no pre-processing of a visual image in order to analyze the visual image. The convolutional neural network may analyze the visual image based on input taken in a patch by patch sequence from the visual image. As shown, the convolutional neural network comprises an input layer 704 configured to receive information about the image 702 (e.g., pixel values for all or one or more portions of a pathology image), an output layer 708 configured to provide the output (e.g., a classification), and a plurality of hidden layers 706 connected between the input layer 704 and the output layer 708. The plurality of hidden layers 706 include convolution and pooling layers 710 and fully connected layers 712.

The input layer 704 may be followed by one or more convolution and pooling layers 710. A convolutional layer may comprise a set of filters that are spatially smaller (e.g., have a smaller width and/or height) than the input to the convolutional layer (e.g., the image 702). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 710 may be followed by fully connected layers 712. The fully connected layers 712 may comprise one or more layers each with one or more neurons that receives an input from a previous layer (e.g., a convolutional or pooling layer) and provides an output to a subsequent layer (e.g., the output layer 708). The fully connected layers 712 may be described as "dense" because each of the neurons in a given layer may receive an input from each neuron in a previous layer and provide an output to each neuron in a subsequent layer. The fully connected layers 712 may be followed by an output layer 708 that provides the output of the convolutional neural network. The output may be, for example, an indication of which class, from a set of classes, the image 702 (or any portion of the image 702) belongs to. The convolutional neural network may be trained using a stochastic gradient descent type algorithm or another suitable algorithm. The convolutional neural network may continue to be trained until the accuracy on a validation set (e.g., held out images from the training data) saturates or using any other suitable criterion or criteria.

It should be appreciated that the convolutional neural network shown in FIG. 7 is only one example implementation and that other implementations may be employed. For example, one or more layers may be added to or removed from the convolutional neural network shown in FIG. 7. Additional example layers that may be added to the convolutional neural network include: a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Convolutional neural networks may be employed to perform any of a variety of functions described herein. For example, a convolutional neural network may be employed to predict tissue characteristics for a pathology image. It should be appreciated that more than one convolutional neural network may be employed to make predictions in some embodiments. For example, a first convolutional neural network may be trained on a set of annotated pathology images and a second, different convolutional neural network may be trained on the same set of annotated pathology images, but magnified by a particular factor, such as 5×, 10×, 20×, or another suitable factor. The first and second neural networks may comprise a different arrangement of layers and/or be trained using different training data.

An example implementation of a convolutional neural network is illustrated below in Table 1. The convolutional neural network shown in Table 1 may be employed to classify an input image (e.g., a pathology image). For example, the convolutional network shown in Table 1 may be configured to receive an input pathology image of size 217 pixels by 217 pixels and provide an output that is indicative of one or more tissue characteristics or labels for the pathology image, e.g., four to eight tissue characteristics or labels. In Table 1, the sequence of the layers is denoted by the "Layer Number" column, the type of the layer is denoted by the "Layer Type" column, and the input to the layer is denoted by the "Input to Layer" column.

TABLE 1

Example Layer Configuration for Convolutional neural network

| Layer Number | Layer Type | # Filters/ Units | Filter Size | Stride | Activation Function | Drop-out | Input to Layer |
|---|---|---|---|---|---|---|---|
| 1 | Input Layer | | | | | | Input Image |
| 2 | Convolution Layer | 96 | 7 | 3 | ReLU | | Output of Layer 1 |
| 3 | Pooling Layer | | 3 | 2 | | | Output of Layer 2 |
| 4 | Convolution Layer | 256 | 5 | 1 | ReLU | | Output of Layer 3 |
| 5 | Pooling Layer | | 3 | 2 | | | Output of Layer 4 |
| 6 | Convolution Layer | 384 | 3 | 1 | ReLU | | Output of Layer 5 |
| 7 | Convolution Layer | 384 | 3 | 1 | ReLU | | Output of Layer 6 |
| 8 | Convolution Layer | 256 | 3 | 1 | ReLU | | Output of Layer 7 |
| 9 | Pooling Layer | | 3 | 2 | ReLU | | Output of Layer 8 |
| 10 | Fully Connected Layer | 2048 | | | ReLU | dropout (0.5) | Output of Layer 9 |
| 11 | Fully Connected Layer | 2048 | | | ReLU | dropout (0.5) | Output of Layer 10 |
| 12 | Fully Connected Layer | # labels | | | softmax | | Output of Layer 11 |

Another example implementation of a convolutional neural network is illustrated below in Table 2. The convolutional neural network shown in Table 2 may be configured to receive an input pathology image of size 97 pixels by 97 pixels and provide an output that is indicative of one or more tissue characteristics or labels for the pathology image, e.g., four to eight tissue characteristics or labels. In Table 2, the sequence of the layers is denoted by the "Layer Number" column, the type of the layer is denoted by the "Layer Type" column, and the input to the layer is denoted by the "Input to Layer" column.

TABLE 2

Example Layer Configuration for Convolutional neural network

| Layer Number | Layer Type | # Filters/ Units | Filter Size | Stride | Activation Function | Drop-out | Input to Layer |
|---|---|---|---|---|---|---|---|
| 1 | Input Layer | | | | | | Input Image |
| 2 | Convolution Layer | 96 | 7 | 3 | ReLU | | Output of Layer 1 |
| 3 | Pooling Layer | | 3 | 2 | | | Output of Layer 2 |

TABLE 2-continued

Example Layer Configuration for Convolutional neural network

| Layer Number | Layer Type | # Filters/ Units | Filter Size | Stride | Activation Function | Dropout | Input to Layer |
|---|---|---|---|---|---|---|---|
| 4 | Convolution Layer | 256 | 5 | 1 | ReLU | | Output of Layer 3 |
| 5 | Pooling Layer | | 3 | 1 | | | Output of Layer 4 |
| 6 | Convolution Layer | 256 | 3 | 1 | ReLU | | Output of Layer 5 |
| 7 | Convolution Layer | 256 | 3 | 1 | ReLU | | Output of Layer 6 |
| 8 | Convolution Layer | 256 | 3 | 1 | ReLU | | Output of Layer 7 |
| 9 | Pooling Layer | | 3 | 2 | | | Output of Layer 8 |
| 10 | Fully Connected Layer | 1024 | | | ReLU | dropout (0.5) | Output of Layer 9 |
| 11 | Fully Connected Layer | 1024 | | | ReLU | dropout (0.5) | Output of Layer 10 |
| 12 | Fully Connected Layer | # labels | | | softmax | | Output of Layer 11 |

In some embodiments, the convolutional neural network does not include padding between layers. The layers may be designed such that there is no overflow as pooling or convolution operations are performed. Moreover, layers may be designed to be aligned. For example, if a layer has an input of size N*N, and has a convolution filter of size K, with stride S, then (N−K)/S must be an integer in order to have perfect alignment.

In some embodiments, the output of the training process is a set of neural networks. For example, the output of the training process are neural networks for different tasks, e.g., identifying cells or identifying regions. In another example, the neural networks are trained at different magnification factors. A network configured to process smaller patches than another network has access to a smaller portion of the image and hence has less context for predicting a particular point annotation for the patches being processed. Combining the output of the network configured to process smaller patches with an output of a network that considers larger portions of the image for annotation may improve the annotation prediction due to the context that the large portion of the image provides. For example, patches extracted from 20× magnification and/or from 5×, 10× and 20× magnification for a particular pathology image may be used to capture different types of features and context about where the cells/regions are located within the image. In some embodiments, each of the networks at different magnification factors may be trained independently and the heat maps may be combined using a logical operation (e.g., a logical AND operation or a logical OR operation). In some embodiments, another network may be trained on the outputs of each of the networks at different magnification factors in order to combine the outputs.

In some embodiments, the network is trained on patches along with one or more features that describe the context of the corresponding patch. For example, the features may include the (x,y) coordinates of the patch, the distance of the patch to the nearest patch having a background category, and other suitable contextual information. In some embodiments, output from a network trained to predict polygon annotations is provided as input to a network being trained to predict point annotations. The output from the network trained to predict polygon annotations may be used to provide context to the point annotation training data being used to train the network to predict point annotations.

Figure 8:
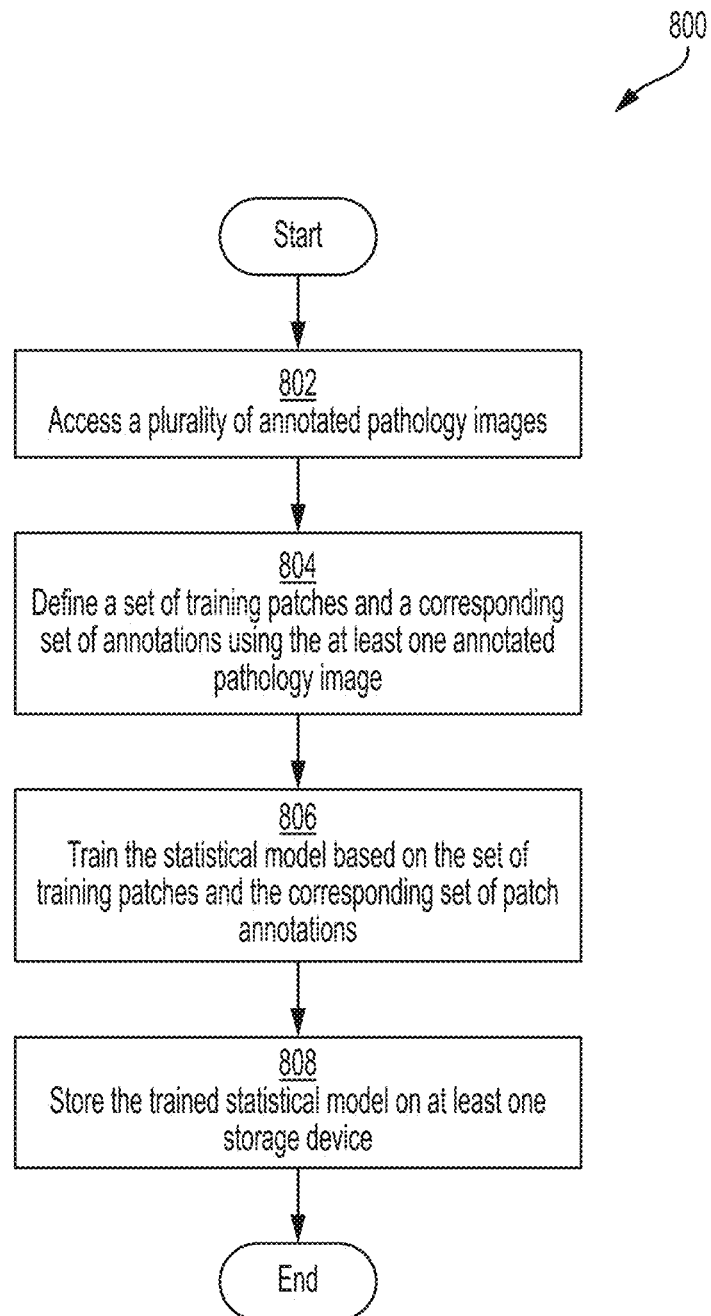
FIGS. 8-9 show illustrative flowcharts for training a statistical model to predict tissue characteristics for a pathology image in accordance with some embodiments of the technology described herein.
Figure 9:
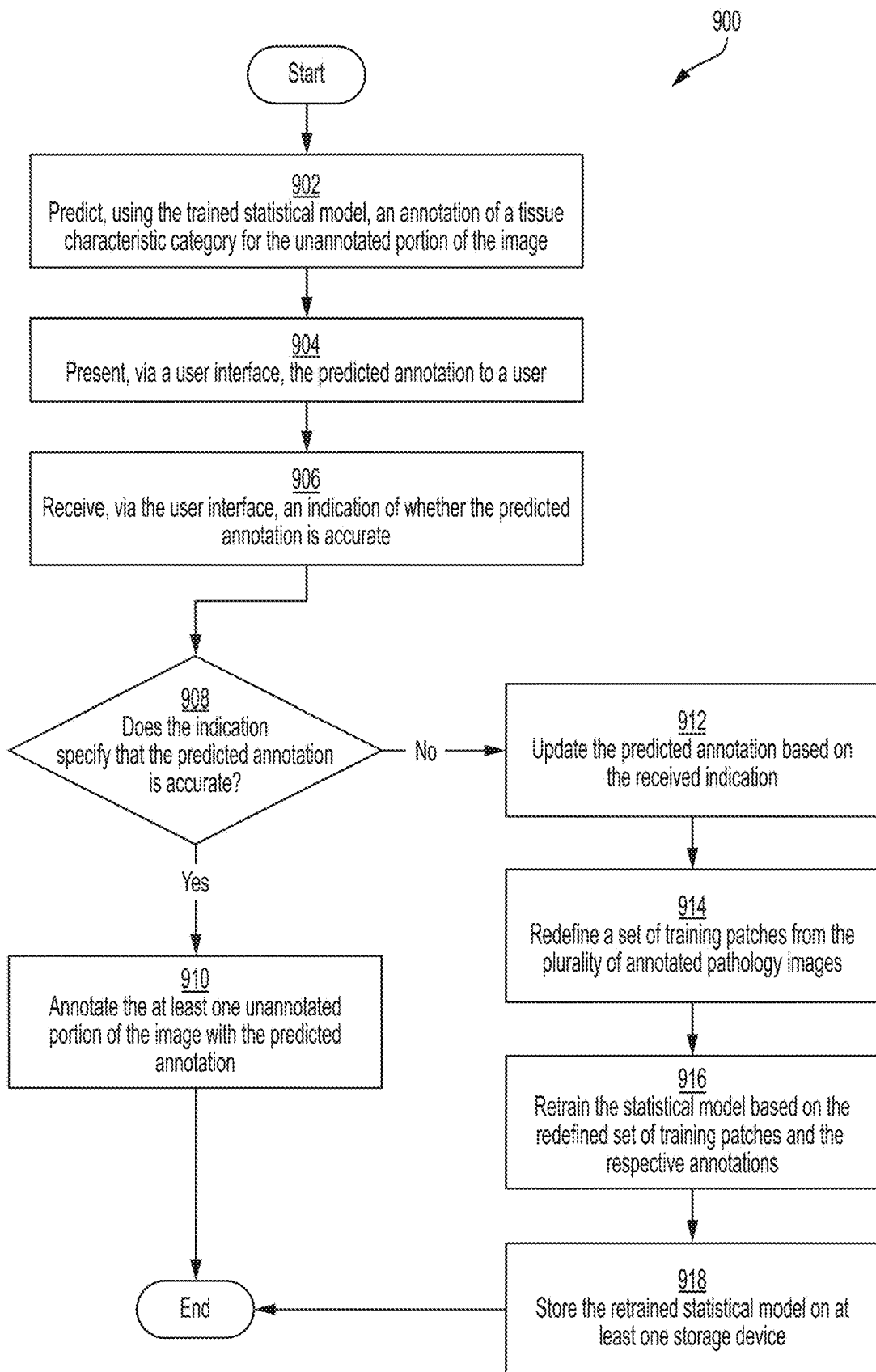

FIGS. 8-9 show illustrative flowcharts for training a statistical model to predict tissue characteristics for a pathology image in accordance with some embodiments of the technology described herein.

Flowchart 800 illustrates an exemplary process for training a statistical model to predict one or more annotations for a pathology image. In flowchart 800, at act 802, annotated pathology images are accessed. Each image includes at least one annotation describing a tissue characteristic category for a portion of the image. For example, an image, such as the image 200, may include an annotation, such as the annotation 204, describing a tissue characteristic category, such as the category cancer epithelium. At act 804, a set of training patches and a corresponding set of annotations is defined using at least one annotated pathology image. Each training patch in the set includes values obtained from a respective subset of pixels in the annotated pathology image and is associated with a corresponding patch annotation determined based on an annotation associated with the subset of pixels. For example, a training patch, such as the training patch 202, may be defined from the image 200. The size of the training patch 202 may be selected to be a size suitable for training the statistical model. The training patch 202 includes the corresponding annotation 204. At act 806, the statistical model is trained based on the set of training patches and the corresponding set of patch annotations. For example, the statistical model, such as a convolutional neural network, may be trained as described with respect to FIG. 6 and FIG. 7. The training data for the statistical model may include the training patch 202 and the corresponding annotation 204. At act 808, the trained statistical model is stored on a storage device.

Flowchart 900 illustrates an exemplary process for receiving validation on predicted annotations of the trained statistical model from, e.g., a pathologist, and retraining the statistical model if the predicted annotations are indicated to be inaccurate. In flowchart 900, at act 902, an annotation of a tissue characteristic category is predicted for an unannotated portion of the image. The predicted annotation may be obtained from processing an unannotated portion of an annotated pathology image using the trained statistical model. For example, as described with respect to FIG. 6, the trained statistical model may be used to associate annotations for part or all of the pathology image using the predicted annotations, with the resultant annotated image being represented as a heat map, an example of which is shown in FIG. 5. At act 904, the predicted annotation is presented via a user interface to a user. For example, the predicted annotation may be presented to a pathologist within a user interface of a computer system for reviewing such annotations. At act 906, an indication of whether the predicted annotation is accurate is received via the user interface. For example, the pathologist reviewing the predicted annotation may enter a confirmation that the predicted annotation is accurate using the user interface of the computer system. In another example, the pathologist may enter a different tissue category for the predicted annotation and/or draw a corrected polygon for the predicted annotation using the user interface of the computer system. At act 908, it is determined whether the indication specifies that the predicted annotation is accurate. If it is determined that the indication specifies that the predicted annotation is accurate, at act 910, the unannotated portion of the image is annotated with the predicted annotation. For example, the unannotated portion of the image may be associated with the predicted annotation, and the association may be stored in a storage device. If it is determined that the indication specifies that the predicted annotation is not accurate, at act 912, the predicted annotation is updated based on the received indication. For example, the category of the predicted annotation may be updated based on the indication. The information related to the updated annotation may be supplied as updated training data for retraining the statistical model. At act 914, a set of training patches is redefined from the annotated pathology images. At act 916, the statistical model is retrained based on the redefined set of training patches and the respective annotations. At act 918, the retrained statistical model is stored on the storage device.

Figure 10:
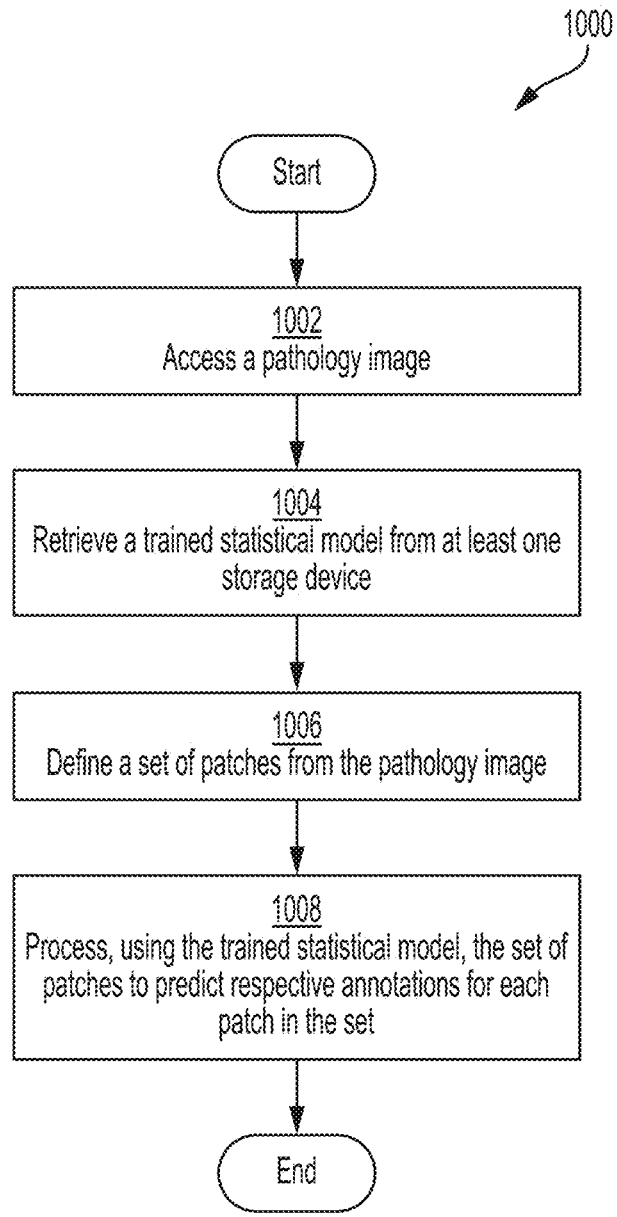
FIG. 10 shows an illustrative flowchart for predicting tissue characteristics for a pathology image using a statistical model in accordance with some embodiments of the technology described herein.

FIG. 10 shows a flowchart 1000 of an illustrative process for predicting tissue characteristics for a pathology image using a statistical model in accordance with some embodiments of the technology described herein. The statistical model may be trained, for example, on annotated pathology images, each of which includes at least one annotation describing tissue characteristics for one or more portions of the image. At act 1002, a pathology image to be analyzed is accessed. At act 1004, a trained statistical model is retrieved from a storage device. The statistical model may be trained on a set of training patches and a corresponding set of patch annotations derived from at least one annotated pathology image. For example, the trained statistical model may be trained as described with respect to FIG. 8 and/or FIG. 9. Each training patch in the set may include values obtained from a respective subset of pixels in the annotated pathology image and is associated with a corresponding patch annotation determined based on an annotation associated with the respective subset of pixels. At act 1006, a set of patches is defined from the pathology image. Each patch in the set may include a subset of pixels from the corresponding pathology image. At act 1008, the set of patches is processed using the trained statistical model to predict respective annotations for each patch in the set. The predicted annotations may be stored on the storage device.

In some aspects, after a convolutional neural network has been trained, the trained statistical model may be applied to partially or fully annotate a pathology image, and features (e.g., distances between annotated lymphocyte pairs in the image) may be extracted from the annotated image. In some embodiments, a function is applied to the annotated pathology image to extract a feature of interest. For example, the feature of interest may be the average distance of lymphocytes to cancer cells in a cancer tumor region of the pathology image. The trained statistical model may be applied to fully annotate the pathology image with predicted lymphocyte annotations and predicted cancer cell annotations. In some embodiments, the trained statistical model generates a single annotated pathology image (or heat map) with both predicted lymphocyte annotations and predicted cancer cell annotations. In some embodiments, the trained statistical model generates one annotated pathology image for predicted lymphocyte annotations and another annotated pathology image for predicted cancer cell annotations. Subsequently, a function may be applied to the fully annotated pathology image(s) to extract the feature. The function may locate the lymphocyte annotations present in the cancer tumor region, determine the distance (e.g., in microns, pixels, or another suitable metric) to the nearest cancer cell annotation (e.g., the cancer cell's nucleus) for each lymphocyte annotation, and average all the determined distances.

In some embodiments, any number and types of features may be extracted from an annotated image. For example, multiple features may be extracted from annotated images of hematoxylin and eosin stain (H&E) and immunohistochemistry (IHC) stained slides, and corresponding feature values may be used to calculate values for other features through combination of one or more of the extracted features. A non-limiting representative list of such features includes area of epithelium, area of stroma, area of necrosis, area of cancer cells, area of macrophages, area of lymphocytes, number of mitotic figures, average nuclear grade, average distance between fibroblasts and lymphocytes, average distance between immunohistochemistry-positive macrophages and cancer cells, standard deviation of nuclear grade, average distance between blood vessels and tumor cells. Other suitable features may include features related to spatial distribution of cells, heterogeneity, and texture.

The extracted features may be used to predict entities of interest, e.g., survival time, drug response, patient level phenotype/molecular characteristics, mutational burden, tumor molecular characteristics (including genomic features (e.g., tumor mutational burden)), transcriptomic features (e.g., RNA signatures), protein expression features (e.g., CD8+ T lymphocyte)), patient clinical outcomes (e.g., prognosis, drug response, and diagnosis), and other suitable entities of interest. The entities may be input into a model, such as a generalized linear model, a random forest, a support vector machine, a gradient boosted tree, or another suitable model, for predicting entities of interest.

In some embodiments, one or more features are extracted from the heat maps generated from the statistical model applied to pathology images. In one example, the pathology images may have been collected from patients having participated in a clinical trial (e.g., a randomized controlled trial for an experimental therapeutic). In a randomized controlled trial, each patient is assigned to receive either the experimental treatment (e.g., which may include a single drug or combination of drugs) or the control treatment (e.g., a placebo). Clinical metadata associated with the patients in the clinical trial including, for example, treatment group, overall survival time, progression free survival time, and best objective response may be received. A model may be trained to predict patient survival outcomes from pathology image data (e.g., features extracted from annotated pathology data) provided as input to the model during training and survival data (e.g., as output of the model) for patients who received the experimental treatment. In some embodiments, the model is trained on features extracted from annotated pathology data along with other clinical metadata values, such as age, gender, clinical measurements, predicted diagnosis by pathologist, etc. These additional values may provide the model with more information on the patient and help improve prediction.

In some embodiments, a model may be trained to predict patient survival outcomes from pathology image data (e.g., features extracted from annotated pathology data) and genomic data (e.g., tumor mutational burden (TMB)) provided as input to the model during training and survival data provided as output of the model. In some embodiments, the model may be trained on transcriptomic and/or protein expression data that is used instead of or in addition to the genomic data.

In some embodiments, the genomic data, e.g., TMB, may be readily available and received with the pathology image data. In some embodiments, the genomic data, e.g., TMB, may not be available and may be predicted using a statistical model trained on pathology images and associated genomic data. The statistical model may be trained in a similar manner as described with respect to FIG. 8. The predicted genomic data may be used to train the model for predicting patient survival outcomes in a similar manner as described above and with respect to FIG. 13. In some embodiments, the statistical model may be trained to predict transcriptomic and/or protein expression data instead of or in addition to the genomic data.

Figure 11:
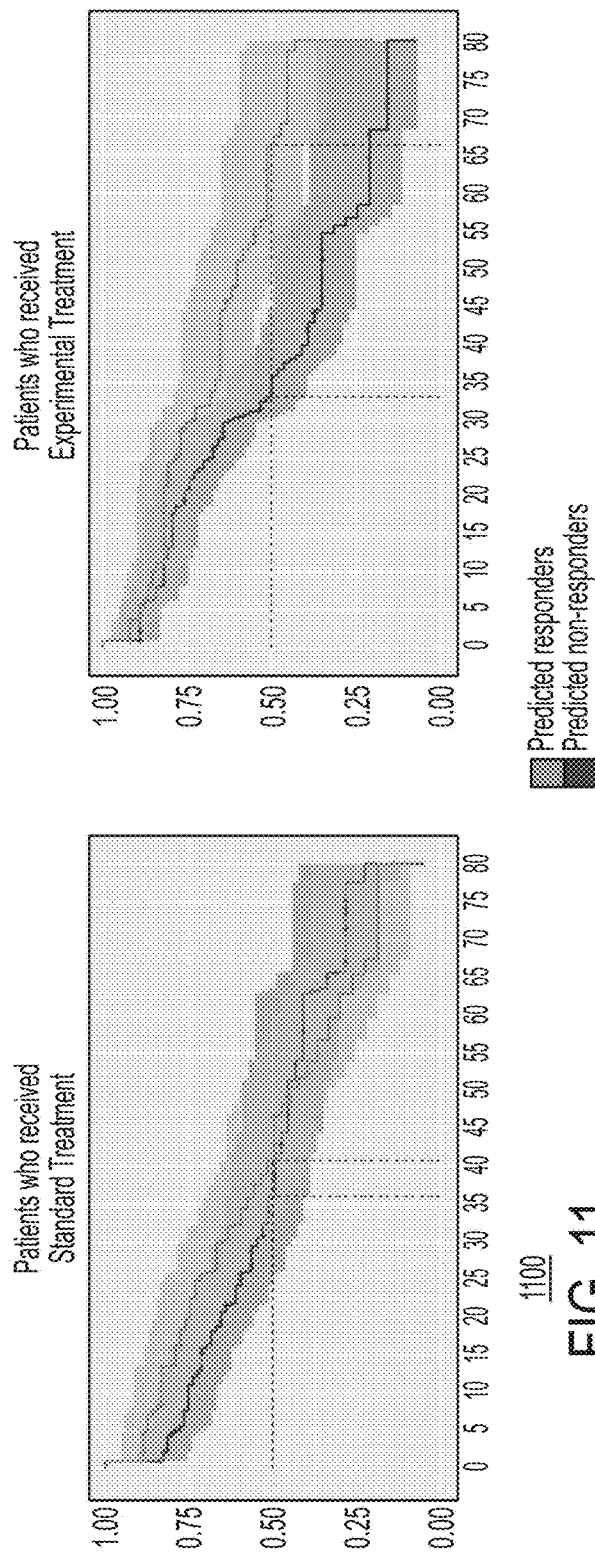
FIGS. 11-12 show illustrative subset survival analyses in accordance with some embodiments of the technology described herein.
Figure 12:
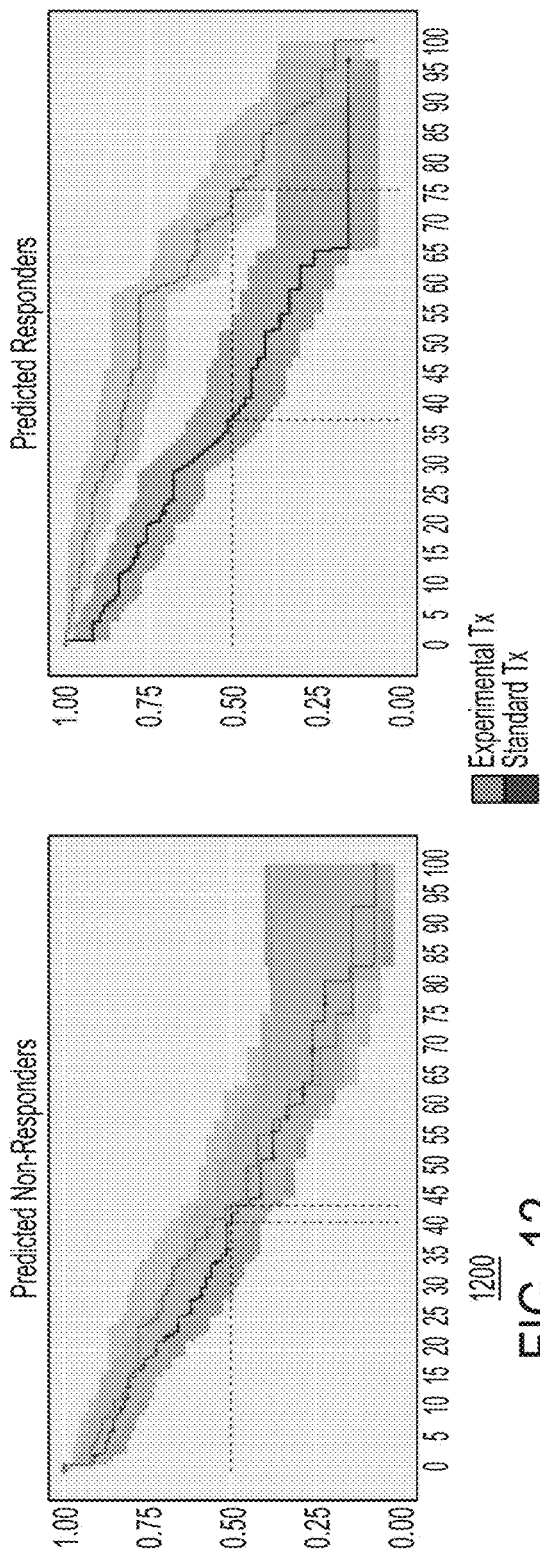

FIGS. 11-12 show illustrative subset survival analyses in accordance with some embodiments of the technology described herein. In some embodiments, to determine the specificity of the model's prognostic power for patients receiving the experimental treatment, the model, trained on survival data associated with images (or features extracted from images) for the patients that received experimental treatment, is used to predict survival data based on images (or features extracted from images) for patients that received the control treatment.

In some embodiments, the predicted survival data is sorted into a "Predicted Responder" group of patients expected to respond to the treatment (experimental or control) and a "Predicted Non-Responder" group of patients expected to not respond to the treatment (experimental or control). In order to determine the specificity of the model's prognostic predictions, a hazard ratio and a 95% confidence interval may be computed for the "Predicted Responder" and "Predicted Non-Responder" groups among patients receiving the experimental treatment. It may then be determined whether the confidence interval includes the hazard ratio of the "Predicted Responder" and "Predicted Non-Responder" groups among the patients that received the control treatment. If the confidence interval does not include the hazard ratio among the patients that received the control treatment, it may be inferred that the prognostic power of the predictive model is specific for the experimental treatment. The hazard ratio is defined as the ratio of the hazard rates corresponding to the experimental treatment and the control treatment. For example, patients receiving the control treatment may not survive at twice the rate per unit time as the patients receiving the experimental treatment.

In some embodiments, the model's prognostic performance for patients that received the experimental treatment is compared to the model's prognostic performance for patients who received the standard or control treatment (1100, FIG. 11). In some embodiments, to determine the prognostic performance of a model, the survival difference between the two groups of patients, the "Predicted Responder" group and "Predicted Non-Responder" group, is assessed by computing a log-rank P-value and a hazard ratio for the hazard rates in the two groups of patients.

In some embodiments, to determine whether the model accurately identifies a patient subset that is likely to benefit from the experimental treatment compared to the standard or control treatment, subset survival analyses are performed to compare survival outcomes of the experimental treatment or control treatment among patients predicted by the model to respond to the experimental treatment. These results are compared to those obtained among patients predicted by the model to not respond to the experimental treatment (1200, FIG. 12). In some embodiments, the predicted survival data is sorted into a "Experimental Tx" group of patients receiving experimental treatment (including predicted responders and predicted non-responders) and a "Standard Tx" group of patients receiving the standard or control treatment (including predicted responders and predicted non-responders). In order to determine the ability of the model to identify a subset of patients that benefits from the experimental treatment, the hazard ratio and 95% confidence interval for the "Experimental Tx" and "Standard Tx" groups among the patients classified by the model to be predicted responders may be computed. It may then be determined whether the confidence interval includes the hazard ratio of the "Experimental Tx" and "Standard Tx" groups among the patients classified by the model as to be predicted non-responders. If the confidence interval does not include the hazard ratio among the predicted non-responders, it may be inferred that the model identifies a subset of patients that benefits from the experimental treatment.

In some embodiments, patient response to an experimental or control treatment includes an objective response status (e.g., complete response, partial response, no response, progressive disease), overall survival time within a threshold (e.g., deceased within five years or alive at least 5 years), or another suitable indicator of patient response.

In some embodiments, machine learning methods are used to predict patient survival from pathology image data and patient survival data. A statistical model, trained using image data and pathologist "polygon" or "point" annotations, is used to label cells and tissue regions in a pathology image using, for example, the techniques described above. A feature vector of human-interpretable features is extracted from each pathology image. A prognostic model is trained using any number of machine learning algorithms (e.g., regularized Cox regression, regularized logistic regression, random forest, support vector machines, etc.) based on the extracted feature values and the patient survival time. The performance of the trained model may be tested by applying the model to extracted features from a pathology image for a new patient to make a survival prediction on the new patient.

In a particular example, overall survival time is used for the survival data. A classifier, such as for example, an L1-regularized logistic regression, is trained to predict the binary outcome of (1) alive at 5 years or (2) dead at 5 years. The Lambda parameter that controls model sparsity is tuned using leave-one-out cross validation. This training and testing may be performed using cross-validation only and/or using an independent set of samples for each of training and testing. The training set may include about 200 samples, and the test set may include about 100 samples. Kaplan Meier curves may be used to compare the survival distributions of the predicted high-risk patients vs. the predicted low-risk patients. The statistical significance of the survival curves may be assessed on the test cases (or held-out cases in the case of cross-validation).

In some embodiments, the prognostic model described above may be generalized in the setting where a prognostic model is trained for each of a number of different treatments (e.g., 10 different prognostic models may be trained on the data from 10 different completed randomized clinical trials). Then, for pathology images from a new sample, all 10 models may be applied to the new sample, resulting in 10 different survival predictions. The treatment with the longest predicted survival time (e.g., given an acceptable side effect profile/cost/etc.) may be recommended. Similarly, this approach may be used to recommend one or more pharmacological agents and/or predict doses for treating an individual patient.

Figure 13:
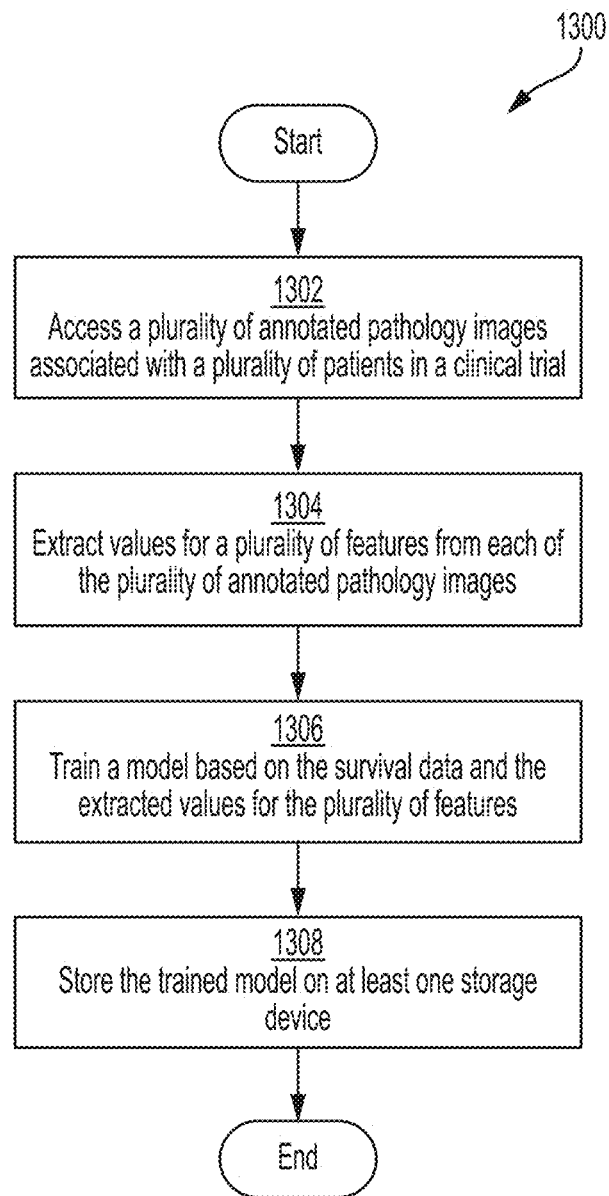
FIG. 13 shows an illustrative flowchart for training a model to predict survival time for a patient in accordance with some embodiments of the technology described herein.

FIG. 13 shows an illustrative flowchart 1300 for training a model to predict survival time for a patient in accordance with some embodiments of the technology described herein. At act 1302, annotated pathology images associated with a group of patients in a clinical trial are accessed. Each annotated pathology image may be associated with survival data for a respective patient. Each annotated pathology image may include at least one annotation describing a tissue characteristic category for a portion of the image. For example, after a convolutional neural network has been trained as described with respect to FIG. 6 and FIG. 7, the trained network may be applied to partially or fully annotate a pathology image. In another example, the annotations for the pathology image may be received from a pathologist or other medical professional. At act 1304, values for one or more features are extracted from each annotated pathology image. For example, the features may be extracted from annotated images of hematoxylin and eosin stain (H&E) and immunohistochemistry (IHC) stained slides, and corresponding feature values may be used to calculate values for other features through combination of one or more of the extracted features. At act 1306, a model is trained based on the survival data and the extracted values for the features. Alternatively or additionally, the model may be trained to predict other predict entities of interest, such as drug response, patient level phenotype/molecular characteristics, mutational burden, tumor molecular characteristics (including genomic features (e.g., tumor mutational burden)), transcriptomic features (e.g., RNA signatures), protein expression features (e.g., CD8+ T lymphocyte)), patient clinical outcomes (e.g., prognosis, drug response, and diagnosis), and other suitable entities of interest. At act 1308, the trained model is stored on a storage device.

Figure 14:
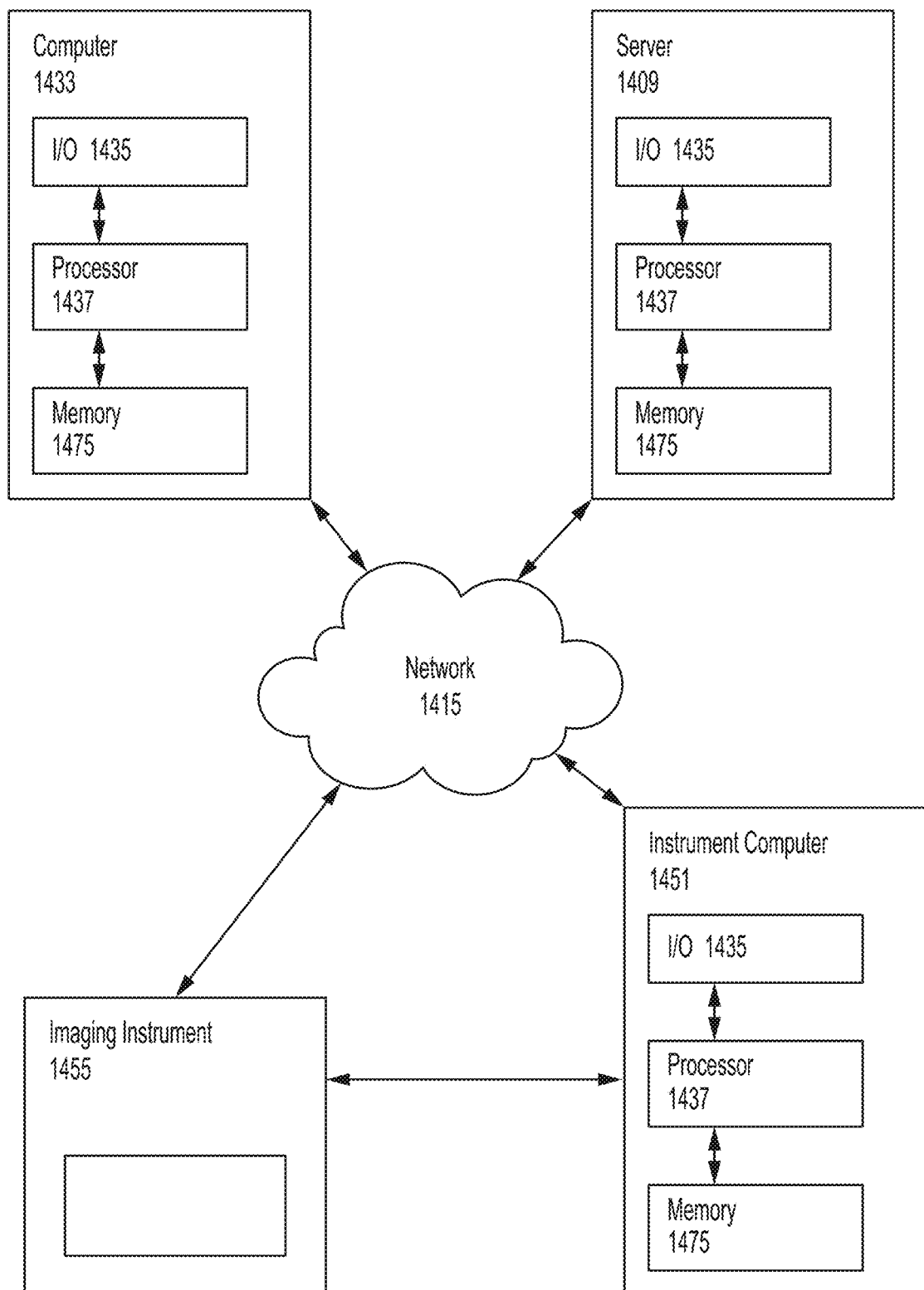
FIG. 14 shows a block diagram of a computer system on which various embodiments of the technology described herein may be practiced.

FIG. 14 shows a block diagram of a computer system on which various embodiments of the technology described herein may be practiced. The system 1400 includes at least one computer 1433. Optionally, the system 1400 may further include one or more of a server computer 1409 and an imaging instrument 1455 (e.g., one of the instruments described above), which may be coupled to an instrument computer 1451. Each computer in the system 1400 includes a processor 1437 coupled to a tangible, non-transitory memory device 1475 and at least one input/output device 1435. Thus the system 1400 includes at least one processor 1437 coupled to a memory subsystem 1475 (e.g., a memory device or collection of memory devices). The components (e.g., computer, server, instrument computer, and imaging instrument) may be in communication over a network 1415 that may be wired or wireless and wherein the components may be remotely located or located in close proximity to each other. Using those components, the system 1400 is operable to receive or obtain training data such as tissue images and outcome data as well as test sample images generated by the imaging instrument or otherwise obtained. In certain embodiments, the system uses the memory to store the received data as well as the model data which may be trained and otherwise operated by the processor.

In some embodiments, some or all of system 1400 is implemented in a cloud-based architecture. The cloud-based architecture may offer on-demand access to a shared pool of configurable computing resources (e.g. processors, graphics processors, memory, disk storage, network bandwidth, and other suitable resources). A processor in the cloud-based architecture may be operable to receive or obtain training data such as tissue images and outcome data as well as test sample images generated by the imaging instrument or otherwise obtained. A memory in the cloud-based architecture may store the received data as well as the model data which may be trained and otherwise operated by the processor. In some embodiments, the cloud-based architecture may provide a graphics processor for training the model in a faster and more efficient manner compared to a conventional processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an NVidia Tesla K80 graphics card from NVIDIA Corporation (Santa Clara, Calif.). A processor may be provided by a chip from Intel or AMD. A processor may be any suitable processor such as the microprocessor sold under the trademark XEON E5-2620 v3 by Intel (Santa Clara, Calif.) or the microprocessor sold under the trademark OPTERON 6200 by AMD (Sunnyvale, Calif.). Computer systems may include multiple processors including CPUs and or GPUs that may perform different steps of the described methods. The memory subsystem 1475 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Each computer may include a non-transitory memory device such as a solid state drive, flash drive, disk drive, hard drive, subscriber identity module (SIM) card, secure digital card (SD card), micro SD card, or solid state drive (SSD), optical and magnetic media, others, or a combination thereof. Using the described components, the system 1400 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

References and citations to other documents, such as patents, patent applications, patent publications, journals, books, papers, web contents, have been made throughout this disclosure and in any patent applications incorporated by reference herein. All such documents are hereby incorporated herein by reference in their entirety for all purposes.

What is claimed is:

1. A method for predicting an entity of interest for a pathology image, the method comprising:
   accessing a pathology image;
   retrieving a first trained statistical model from at least one storage device, wherein the first trained statistical model is trained on a plurality of annotated pathology images, wherein each image of the plurality of annotated pathology images includes at least one annotation describing tissue characteristics for one or more portions of the image;
   processing, using the first trained statistical model, the pathology image to generate an annotated pathology image including one or more annotations for the pathology image;
   extracting values for one or more features from the annotated pathology image;
   retrieving a second trained statistical model from the at least one storage device, wherein the second trained statistical model is trained on extracted values for the one or more features from the plurality of annotated pathology images;
   processing, using the second trained statistical model, the values for the one or more features extracted from the annotated pathology image to predict an entity of interest, wherein the entity of interest is selected from a group consisting of survival time, drug response, patient level phenotype/molecular characteristics, mutational burden, tumor molecular characteristics, transcriptomic features, protein expression features, and patient clinical outcomes; and
   storing the predicted entity of interest on the at least one storage device.

2. The method of claim 1, wherein the first trained statistical model comprises a convolutional neural network including a plurality of layers, wherein there is no padding applied to an output of any layer of the plurality of layers.

3. The method of claim 1, wherein the first trained statistical model comprises a convolutional neural network including a plurality of layers, wherein at least one layer of the plurality of layers is aligned such that (N–K)/S is an integer, wherein N represents a size of each input dimension of the at least one layer, wherein K represents a size of a convolution filter of the at least one layer, and wherein S represents a size of a stride of the at least one layer.

4. The method of claim 1, wherein processing, using the first trained statistical model, the pathology image to generate the annotated pathology image including the one or more annotations for the pathology image comprises:
   associating one or more portions of the pathology image with the predicted one or more annotations; and
   storing the associations of the one or more portions of the pathology image with the predicted one or more annotations on the at least one storage device.

5. The method of claim 1, wherein the one or more features are selected from a group consisting of area of epithelium, area of stroma, area of necrosis, area of cancer cells, area of macrophages, area of lymphocytes, number of mitotic figures, average nuclear grade, average distance between fibroblasts and lymphocytes, average distance between immunohistochemistry-positive macrophages and cancer cells, standard deviation of nuclear grade, average distance between blood vessels and tumor cells.

6. The method of claim 1, wherein the second trained statistical model comprises a generalized linear model, a random forest, a support vector machine, and/or a gradient boosted tree.

7. The method of claim 1, wherein extracting the values for the one or more features from the annotated pathology image comprises applying one or more functions to the annotated pathology image to extract the values for the one or more features.

8. The method of claim 1, further comprising determining a first value for a first feature based on a combination of at least some of the values for the one or more features.

9. The method of claim 1, wherein the annotated pathology image includes a heat map.

10. The method of claim 9, wherein extracting the values for the one or more features from the annotated pathology image comprises applying one or more functions to the heat map to extract the values for the one or more features.

11. A system for predicting an entity of interest for a pathology image, the system comprising:
    at least one computer hardware processor; and
    at least one non-transitory computer-readable storage medium storing processor-executable instructions that, when executed by the at least one computer hardware processor, cause the at least one computer hardware processor to perform:
       accessing a pathology image;
       retrieving a first trained statistical model from at least one storage device, wherein the first trained statistical model is trained on a plurality of annotated pathology images, wherein each image of the plurality of annotated pathology images includes at least one annotation describing tissue characteristics for one or more portions of the image;
       processing, using the first trained statistical model, the pathology image to generate an annotated pathology image including one or more annotations for the pathology image;
       extracting values for one or more features from the annotated pathology image;
       retrieving a second trained statistical model from the at least one storage device, wherein the second trained statistical model is trained on extracted values for the one or more features from the plurality of annotated pathology images;
       processing, using the second trained statistical model, the values for the one or more features extracted from the annotated pathology image to predict an entity of interest, wherein the entity of interest is selected from a group consisting of survival time, drug response, patient level phenotype/molecular characteristics, mutational burden, tumor molecular characteristics, transcriptomic features, protein expression features, and patient clinical outcomes; and storing the predicted entity of interest on the at least one storage device.

12. The system of claim 11, wherein the first trained statistical model comprises a convolutional neural network including a plurality of layers, wherein there is no padding applied to an output of any layer of the plurality of layers.

13. The system of claim 11, wherein the first trained statistical model comprises a convolutional neural network including a plurality of layers, wherein at least one layer of the plurality of layers is aligned such that (N−K)/S is an integer, wherein N represents a size of each input dimension of the at least one layer, wherein K represents a size of a convolution filter of the at least one layer, and wherein S represents a size of a stride of the at least one layer.

14. The system of claim 11, wherein processing, using the first trained statistical model, the pathology image to generate the annotated pathology image including the one or more annotations for the pathology image comprises:

associating one or more portions of the pathology image with the predicted one or more annotations; and storing the associations of the one or more portions of the pathology image with the predicted one or more annotations on the at least one storage device.

15. The system of claim 11, wherein the one or more features are selected from a group consisting of area of epithelium, area of stroma, area of necrosis, area of cancer cells, area of macrophages, area of lymphocytes, number of mitotic figures, average nuclear grade, average distance between fibroblasts and lymphocytes, average distance between immunohistochemistry-positive macrophages and cancer cells, standard deviation of nuclear grade, average distance between blood vessels and tumor cells.

16. The system of claim 11, wherein the second trained statistical model comprises a generalized linear model, a random forest, a support vector machine, and/or a gradient boosted tree.

17. The system of claim 11, wherein extracting the values for the one or more features from the annotated pathology image comprises applying one or more functions to the annotated pathology image to extract the values for the one or more features.

18. The system of claim 11, wherein the processor-executable instructions further cause the at least one computer hardware processor to perform determining a first value for a first feature based on a combination of at least some of the values for the one or more features.

19. The system of claim 11, wherein the annotated pathology image includes a heat map.

20. The system of claim 19, wherein extracting the values for the one or more features from the annotated pathology image comprises applying one or more functions to the heat map to extract the values for the one or more features.

* * * * *